(12) United States Patent
Schnorr

(10) Patent No.: US 10,829,750 B2
(45) Date of Patent: *Nov. 10, 2020

(54) POLYPEPTIDES HAVING LYSOZYME ACTIVITY AND POLYNUCLEOTIDES ENCODING SAME

(71) Applicant: Novozymes A/S, Bagsvaerd (DK)

(72) Inventor: Kirk Matthew Schnorr, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/023,129

(22) Filed: Jun. 29, 2018

(65) Prior Publication Data

US 2018/0298365 A1 Oct. 18, 2018

Related U.S. Application Data

(62) Division of application No. 15/495,031, filed on Apr. 24, 2017, now Pat. No. 10,039,300, which is a division of application No. 14/360,508, filed as application No. PCT/EP2012/073493 on Nov. 23, 2012, now Pat. No. 9,663,775.

(60) Provisional application No. 61/564,372, filed on Nov. 29, 2011.

(30) Foreign Application Priority Data

Nov. 25, 2011 (EP) .................................... 11190690

(51) Int. Cl.
| | |
|---|---|
| C12N 9/24 | (2006.01) |
| A23K 20/184 | (2016.01) |
| C12N 9/36 | (2006.01) |
| A23K 40/25 | (2016.01) |
| A23K 40/20 | (2016.01) |
| C11B 1/10 | (2006.01) |
| A23K 20/174 | (2016.01) |
| A23K 20/20 | (2016.01) |
| A23K 50/75 | (2016.01) |
| A23K 50/80 | (2016.01) |
| C11D 3/386 | (2006.01) |
| C12N 15/10 | (2006.01) |
| A23K 20/189 | (2016.01) |
| A61K 38/00 | (2006.01) |

(52) U.S. Cl.
CPC .......... *C12N 9/2462* (2013.01); *A23K 20/174* (2016.05); *A23K 20/184* (2016.05); *A23K 20/189* (2016.05); *A23K 20/20* (2016.05); *A23K 40/20* (2016.05); *A23K 40/25* (2016.05); *A23K 50/75* (2016.05); *A23K 50/80* (2016.05); *C11B 1/102* (2013.01); *C11D 3/38636* (2013.01); *C12N 15/1003* (2013.01); *C12Y 302/01017* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,355,022 A | 10/1982 | Rabussy | |
| 5,041,236 A | 8/1991 | Carpenter et al. | |
| 5,376,288 A | 12/1994 | Falholt | |
| 6,710,023 B1 | 3/2004 | Bodet | |
| 7,635,470 B2 | 12/2009 | Wu | |
| 9,663,775 B2 * | 5/2017 | Schnorr | ............... C12N 9/2462 |
| 10,039,300 B2 * | 8/2018 | Schnorr | ............... C12N 9/2462 |
| 2008/0227147 A1 | 9/2008 | Wu | |

FOREIGN PATENT DOCUMENTS

| | | |
|---|---|---|
| EP | 0425016 A2 | 5/1991 |
| GB | 2331750 A | 6/1999 |
| GB | 2379166 A | 3/2003 |
| JP | 2006182662 A | 7/2006 |
| RU | 2232818 C1 | 7/2004 |
| WO | 00/21381 A1 | 4/2000 |
| WO | 02/33041 A2 | 4/2002 |
| WO | 02/064814 A2 | 8/2002 |
| WO | 03/005963 A2 | 1/2003 |
| WO | 2004/017988 A1 | 3/2004 |
| WO | 2004/026334 A1 | 4/2004 |
| WO | 2005/080559 A1 | 9/2005 |
| WO | 2008/124764 A1 | 10/2008 |
| WO | 2009/102755 A1 | 8/2009 |
| WO | 2010/115156 A2 | 10/2010 |
| WO | 2011/104339 A1 | 9/2011 |
| WO | 2013/076253 A1 | 5/2013 |

OTHER PUBLICATIONS

Felsch et al., Journal of Biological Chemistry, vol. 250, No. 10, pp. 3713-3720 (1975).
Fourgoux-Nicol et al., Plant Mol. Biol, vol. 40, pp. 857-872 (1999).
Guo et al., PNAS, vol. 101, pp. 9205-9210 (2004).

(Continued)

*Primary Examiner* — Medina A Ibrahim
(74) *Attorney, Agent, or Firm* — Elias Lambiris

(57) ABSTRACT

The present invention relates to isolated polypeptides having lysozyme activity and polynucleotides encoding the polypeptides. The invention also relates to nucleic acid constructs, vectors, and host cells comprising the polynucleotides as well as methods of producing and using the polypeptides.

14 Claims, 1 Drawing Sheet
Specification includes a Sequence Listing.

(56) References Cited

OTHER PUBLICATIONS

Hughey et al., Applied and Environmental Mictobiology, vol. 53, No. 9, pp. 2165-2170 (1987).
Kimmenade et al., UniProt Accession No. AXQ25767 (2009).
Klosterman et al., UniProt Accession No. G2XHC2 (2011).
Korczynska et al., Acta Crystallographica Section F Strutural Biology and Crystallization Communications, vol. 60, No. 9, pp. 973-977 (2010).
Martinez et al., Nature Biotechnology, vol. 26, No. 5, pp. 553-560 (2008).
Martinez et al., UniProt Accession No. G0RAJ4 (2011).
Masschalck et al., Journal of Food Protection, vol. 65, No. 12, pp. 1916-1923 (2002).
Nierman et al., UniProt Accession No. B8M1A1 (2009).
Paces et al., Accession No. A26215 and J24831 (1986).
Seffernick et al., Journal of Bacteriology, vol. 183, No. 8, pp. 2405-2410 (2001).
Shimonishi et al., Geneseq Accession No. AAX08639 (1999).
Wohlkonig et al., Plos One, vol. 5, No. 11, article e15388, pp. 1-10 (2010).
Maga et al., Transgenic Res., vol. 15, pp. 515-519 (2006).
Oliver et al., Journal of Animal Science and Biotechnology, vol. 6, No. 35, pp. 1-7 (2015).

\* cited by examiner

RDA with 10 µl Lysozymes 0.7ug/ul and 0.35ug/ul spotted against S.carnosus and E.coli
05.10.11
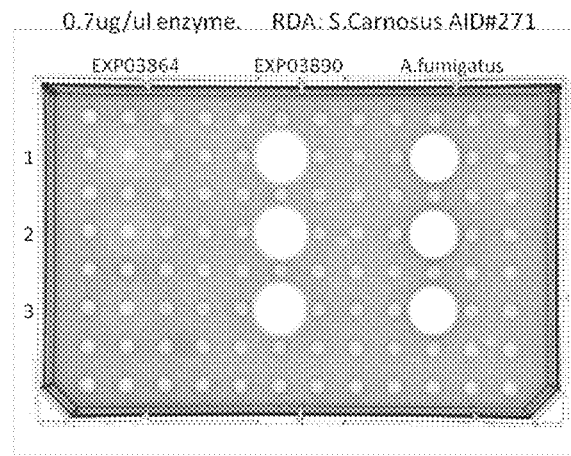
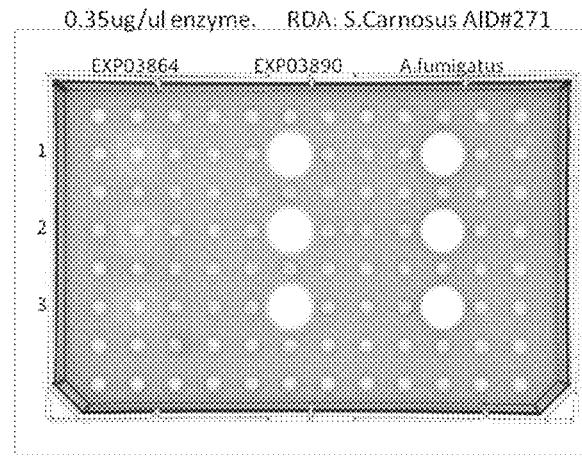
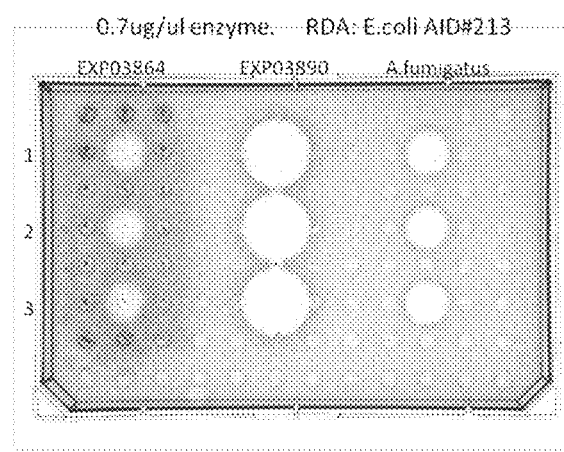
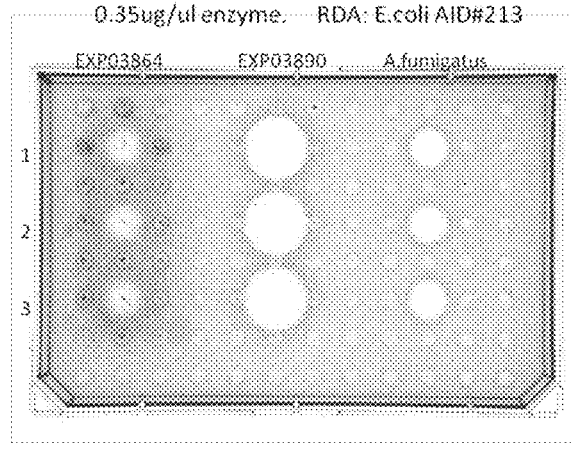

POLYPEPTIDES HAVING LYSOZYME ACTIVITY AND POLYNUCLEOTIDES ENCODING SAME

CROSS-REFERENCE TO RELATED APPLICATIONS

This application is a divisional of U.S. application Ser. No. 15/495,031 filed on Apr. 24, 2017, now U.S. Pat. No. 10,039,300, which is a divisional of U.S. Ser. No. 14/360,508 filed on May 23, 2014, now U.S. Pat. No. 9,663,775, which is a 35 U.S.C. 371 national application of international application no. PCT/EP2012/073493 filed Nov. 23, 2012, which claims priority or the benefit under 35 U.S.C. 119 of European application no. 11190690.5 filed Nov. 25, 2011 and U.S. provisional application No. 61/564,372 filed Nov. 29, 2011. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having lysozyme activity, catalytic domains, and polynucleotides encoding the polypeptides and catalytic domains. The invention also relates to nucleic acid constructs, vectors, and host cells comprising the polynucleotides as well as methods of producing and using the polypeptides and catalytic domains.

Description of the Related Art

Lysozyme is an O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse resulting from osmotic pressure.

Lysozyme occurs in many organisms such as viruses, plants, insects, birds, reptiles and mammals. In mammals, Lysozyme has been isolated from nasal secretions, saliva, tears, intestines, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide.

There is an increasing interest in the potential of lysozyme enzymes as antimicrobial agents. For example, lysozyme activity has been shown against pathogens such as *Streptococcus pneumoniae, Bacillus anthracis, Enterococcus faecium, Bacillus stearothermophilus, Clostridium botulinum, Clostridium butyricum, Clostridium perfringens, Clostridium sporogenes, Clostridium tyrobutyricum*, and *Listeria monocytogenes*.

Lysozyme has been classified into five different glycoside hydrolase (GH) families (CAZy, www.cazy.org): hen egg-white lysozyme (GH22), goose egg-white lysozyme (GH23), bacteriophage T4 lysozyme (GH24), *Sphingomonas* flagellar protein (GH73) and *Chalaropsis* lysozymes (GH25). Lysozymes from the families GH23 and GH24 are primarily known from bacteriophages and have not been identified in fungi. The lysozyme family GH25 has been found to be structurally unrelated to the other lysozyme families.

Use of lysozyme has been suggested in animal feed (see for example WO 00/21381 and WO 2004/026334), in cheese production (see for example WO 2005/080559), food preservation (Hughey and Johnson, 1987, *Appl. Environ. Microbiol.* 53:2165), detergents (see for example U.S. Pat. No. 5,041,236 and EP 0425016), in oral care (see for example U.S. Pat. No. 4,355,022, WO 2004/017988 and WO 2008/124764), cosmetology and dermatology, contraception, urology, and gynaecology (see for example WO 2008/124764).

A GH25 lysozyme has been reported from *Chalaropsis* (Felsch et al., 1975, "The N,O-Diacetylmuramidase of *Chalaropsis* species; V The complete amino acid sequence", *J. Biol. Chem.* 250(10):3713-3720).

Hen egg white lysozyme which is the primary product available on the commercial market, does not cleave N,6-O-diacetylmuramidase in, e.g., *Staphylococcus aureus* cell walls and is thus unable to lyse this important human pathogen among others (Masschalck et al., 2002, "Lytic and nonlytic mechanism of inactivation of gram-positive bacteria by lysozyme under atmospheric and high hydrostatic pressure", *J. Food Prot.* 65(12):1916-23).

It has been observed that different lysozymes have different specificities towards different microorganisms. It is therefore desirable to have several lysozymes available in order to be able to select suitable enzymes for each particular application. New polypeptides having lysozyme activity is therefore desired.

SUMMARY OF THE INVENTION

The present invention related to isolated fungal polypeptides belonging to the GH23 or GH24 families and having lysozyme activity.

The present invention further relates to isolated polypeptides having lysozyme activity selected from the group consisting of:

(a) a polypeptide having at least 90%, at least 91%, at least 92%, at least 93%, at least 94%, at least 95%, at least 96%, at least 97%, at least 98%, at least 99% or 100% sequence identity to the mature polypeptide of SEQ ID NO: 6;

(b) a polypeptide having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2;

(c) a polypeptide having at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 4;

(d) a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1;

(e) a polypeptide encoded by a polynucleotide having at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 3;

(f) a polypeptide encoded by a polynucleotide having at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 5;

(g) a polypeptide encoded by a polynucleotide that hybridizes under medium-high stringency conditions with the mature polypeptide coding sequence of SEQ ID NO: 1, SEQ ID NO: 3 or SEQ ID NO: 5, or the full-length complement of thereof;

(h) a variant of the mature polypeptide of SEQ ID NO: 2, SEQ ID NO: 4 or SEQ ID NO: 6, comprising a substitution, deletion, and/or insertion at one or more (e.g., several) positions; and (i) a fragment of the polypeptide of (a), (b), (c), (d), (e), (f), (g) or (h) that has lysozyme activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to the polypeptides on the invention having antimicrobial activity and methods of use of the polypeptides on the invention as inhibitors of biofilm formation, in detergent compositions, in animal feed and for the extraction of bacterial genomic DNA.

The present invention also relates to a polynucleotide encoding a signal peptide comprising or consisting of amino acids 1 to 19 of SEQ ID NO: 2, amino acids 1 to 20 of SEQ ID NO: 4 or amino acids 1 to 19 of SEQ ID NO: 6, which is operably linked to a gene encoding a protein; nucleic acid constructs, expression vectors, and recombinant host cells comprising the polynucleotides; and methods of producing a protein.

Overview of Sequence Listing

SEQ ID NO: 1 is the DNA sequence of the P8EH GH23 gene as isolated from *Aspergillus aculeatus* CBS 172.66.

SEQ ID NO: 2 is the amino acid sequence as deduced from SEQ ID NO: 1.

SEQ ID NO: 3 is the DNA sequence of the P242MS GH24 gene as isolated from *Acremonium alkalophilum* CBS 114.92.

SEQ ID NO: 4 is the amino acid sequence as deduced from SEQ ID NO: 3.

SEQ ID NO: 5 is the DNA sequence of the P244A7 GH24 gene as isolated from *Acremonium alkalophilum* CBS 114.92.

SEQ ID NO: 6 is the amino acid sequence as deduced from SEQ ID NO: 5.

SEQ ID NO: 7 is the DNA sequence of the P242M9 GH25 gene as isolated from *Acremonium alkalophilum* CBS 114.92.

SEQ ID NO: 8 is the amino acid sequence as deduced from SEQ ID NO: 7.

SEQ ID NO: 9 is the forward primer F-P8EH.
SEQ ID NO: 10 is the reverse primer R-P8EH.
SEQ ID NO: 11 is the forward primer F-P242MS.
SEQ ID NO: 12 is the reverse primer R-P242MS.
SEQ ID NO: 13 is the forward primer F-P244A7.
SEQ ID NO: 14 is the reverse primer R-P244A7.

BRIEF DESCRIPTION OF THE FIGURES

FIG. 1 shows radial diffusion assays of *Acremonium alcalophilum* GH24 lysozyme (EXP03890, SEQ ID NO: 6), *Acremonium alcalophilum* GH25 lysozyme (EXP03864, SEQ ID NO: 8) and a reference lysozyme from *Aspergillus fumigatus* GH25 on *S. carnosus* and *E. coli*.

DEFINITIONS

Lysozyme: The term "lysozyme" activity is defined herein as an O-glycosyl hydrolase, which catalyses the hydrolysis of the glycosidic bond between two or more carbohydrates, or between a carbohydrate and a non-carbohydrate moiety. Lysozymes cleave the glycosidic bond between certain residues in mucopolysaccharides and mucopeptides of bacterial cell walls, such as 1,4-beta-linkages between N-acetylmuramic acid and N-acetyl-D-glucosamine residues in a peptidoglycan and between N-acetyl-D-glucosamine residues in chitodextrins, resulting in bacteriolysis. Lysozyme belongs to the enzyme class EC 3.2.1.17. For purposes of the present invention, lysozyme activity is determined according to the turbidity assay described in example 5. In one aspect, the polypeptides of the present invention have at least 20%, e.g., at least 40%, at least 50%, at least 60%, at least 70%, at least 80%, at least 90%, at least 95%, or at least 100% of the lysozyme activity of the mature polypeptide of one of SEQ ID NO: 2, SEQ ID NO: 4 or SEQ ID NO: 6.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Antimicrobial activity: The term "antimicrobial activity" is defined herein as is an activity that kills or inhibits the growth of microorganisms, such as, algae, archea, bacteria, fungi and/or protozoans. The antimicrobial activity can for example be bactericidal meaning the killing of bacteria or bacteriostatic meaning the prevention of bacterial growth. The antimicrobial activity can include catalyzing the hydrolysis of 1,4-beta-linkages between N-acetylmuramic acid and N-acetyl-D-glucosamine residues in a peptidoglycan and between N-acetyl-D-glucosamine residues in chitodextrins. Antimicrobial activity can also include the lysozyme binding to the surface of the microorganism and inhibiting its growth. The antimicrobial effect can also include the use of the lysozymes of the present invention for activation of bacterial autolysins, as an immunostimulator, by inhibiting or reducing bacterial toxins and by an opsonin effect. For purposes of the present invention, antimicrobial activity is determined according to the radial diffusion assay described in example 4.

Altered/modified property: The term "altered/modified property" is defined herein as a characteristic associated with a variant that is altered or modified, as compared relative to the parent lysozyme or an identified reference sequence. The altered or modified property may be a characteristic associated with a variant that is improved, unless otherwise stated, relative to another reference lysozyme or the parent lysozyme. Examples of properties which can be altered/modified or improved are given below.

Thermostability: The term "thermostability" refers to the lysozyme activity after a period of incubation at elevated temperature relative to the parent or an identified reference sequence, either in a buffer or under conditions such as those which exist during product storage/transport or conditions similar to those that exist during industrial use of the variant.

A variant may or may not display an altered thermal activity profile relative to the parent. In one aspect, the thermostability of the variant having lysozyme activity is at least 1.0-fold, e.g., at least 1.1-fold, at least 1.5-fold, at least 1.8-fold, at least 2-fold, at least 5-fold, at least 10-fold, at least 15-fold, at least 20-fold, and at least 25-fold more thermostable than the parent or reference sequence at the selected temperature. Preferably the activity is tested using the lysozyme turbidity activity assay described in the "Materials and Methods" section.

Temperature profile/temperature stability: The term "temperature profile/temperature stability" refers to the variant enzyme showing a modified temperature profile as compared to the parent or an identified reference sequence, wherein the temperature profile is determined as lysozyme activity as a function of temperature. The activity at each temperature is preferably indicated as relative activity (in %) normalized to the value at optimum temperature. The optimum temperature is that temperature within the tested temperatures (i.e., those with 5-10° C. jumps) where the activity is highest.

pH stability: The term "pH stability" refers to the variant enzyme displaying structural stability relative to the parent lysozyme or an identified reference sequence, after a period of incubation at a pH which is outside the pH range where the enzyme is active (pH activity range). Such a variant may or may not display an altered pH activity profile relative to the parent. For example, the variant may not be active at the increased or decreased pH, but is able to maintain its three dimensional structure and then regain activity once it is returned to the pH activity range. Alternatively, the variant may have an improved ability to refold relative to the parent following incubation at increased or decreased pH.

In one aspect, the pH stability profile is altered such that a lysozyme variant has improved stability at acidic pH. As used herein, acidic pH means from pH 2 to 5.5, preferably from 2.5 to 5.25, more preferably from 3 to 5, even more preferably from 3.5 to 4. Preferably, the variant lysozyme maintains at least 40%, preferably at least 50%, 60%, 70% or 80%, more preferably at least 90%, even more preferably at least 95% residual activity after incubation at a given pH for 1 hour when compared to the variant which has been maintained at pH 6.5 for the same time. Preferably, the residual activity of the variant lysozyme is at least 1.1-fold, at least 1.3-fold, at least 1.5-fold, preferably at least 2-fold, more preferably at least 5-fold, most preferably at least 7-fold, and even most preferably at least 10-fold higher than the residual activity of the parent lysozyme or an identified reference sequence which has been treated under the same conditions. Preferably, the activity is tested using the lysozyme turbidity activity assay described in the "Materials and Methods" section.

pH activity profile: The term "pH activity profile" is defined herein as a variant lysozyme displaying an alteration of the pH-dependent activity profile when compared to the pH activity profile of the parent lysozyme or an identified reference sequence. The pH activity profile provides a measure of the enzyme's efficiency in preventing microbial growth, eliminating microbial cells and/or performing catalysis of a hydrolysis reaction over a pH range at given conditions such as temperature and solvent composition. A lysozyme has a specific pH range wherein the polypeptide is stable and retains its enzymatic activity, outside this range the lysozyme becomes less active and potentially also less stable. Within the pH range there generally is a pH optimum, where the lysozyme shows the highest activity.

A lysozyme variant with improved activity at alkaline pH (e.g., from pH 7.5 to 12, preferably from 8 to 11, more preferably from 8.5 to 10, even more preferably from 9 to 9.5) will be able to function in more alkaline environments such as detergents.

A variant with improved activity at acidic pH (e.g., from pH 2 to 6.5, preferably from 2.5 to 6, more preferably from 3 to 5.5, even more preferably from 3.5 to 5) will be able to function under more acidic conditions, such as preservative in certain foods or as a eubiotic molecule in feeds.

In one aspect, the pH activity profile is altered such that a lysozyme variant has improved activity at a more alkaline pH. Preferably, the activity of the lysozyme variant at a pH at least 0.5 units higher, preferably at least 1.0 pH units higher, more preferably at least 1.5 pH units higher, even more preferably at least 2.0 pH units higher is at least 1.1-fold, preferably at least 1.5-fold, more preferably at least 2-fold, even more preferably at least 5-fold and most preferably at least 10-fold higher than that of the parent enzyme or an identified reference sequence. Preferably, the lysozyme variant at the same time maintains at least 40%, preferably at least 50%, 60%, 70% or 80%, or 90%, more preferably at least 95%, even more preferably at least 100% of the activity that parent lysozyme or an identified reference sequence exhibits at its pH optimum. Preferably, the activity is tested using the lysozyme turbidity activity assay described in the "Materials and Methods" section.

In another aspect, the pH activity profile is altered such that a lysozyme variant has improved activity at a more acidic pH. Preferably, the activity of the lysozyme variant at a pH at least 0.5 units lower, preferably at least 1.0 pH units lower, more preferably at least 1.5 pH units lower, even more preferably at least 2.0 pH units lower is at least 1.1-fold, preferably at least 1.5-fold, more preferably at least 2-fold, even more preferably at least 5-fold and most preferably at least 10-fold higher than that of the parent enzyme or an identified reference sequence. Preferably, the lysozyme variant at the same time maintains at least 40%, preferably at least 50%, 60%, 70% or 80%, or 90%, more preferably at least 95%, even more preferably at least 100% of the activity that parent lysozyme or an identified reference sequence exhibits at its pH optimum. Preferably, the activity is tested using the lysozyme turbidity activity assay described in the "Materials and Methods" section.

Glycation Susceptibility: Non-enzymatic glycation is a spontaneous posttranslational process where reducing sugars bind covalently to free amino groups in proteins primarily at Lysine (K) residues. Glycation may impact the activity of the lysozyme. In accordance with the present invention, the susceptibility of the lysozyme to non-enzymatic glycation may be reduced by specified amino acid changes.

Improved properties may also include thermal properties, such as pelleting stability, steam stability, broader temperature activity profile. Further improved properties may include protease-sensibility, and/or glycosylation pattern. Improvements are preferably assessed in relation to the desired application conditions.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has lysozyme activity. In one aspect, a fragment contains at least 198 amino acid residues (e.g., amino acids 59 to 256 of SEQ ID NO: 2), or at least 230 amino acid residues (e.g., amino acids 32 to 261 of SEQ ID NO: 2). In another aspect, a fragment contains at least 159 amino acid residues (e.g., amino acids 25 to 183 of SEQ ID NO: 4). In a further aspect, a fragment contains at least 150 amino acid residues (e.g., amino acids 24 to 173 of SEQ ID NO: 6).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 264 of SEQ ID NO: 2, amino acids 21 to 186 of SEQ ID NO: 4 or amino acids 20 to 176 of SEQ ID NO: 6 based on the SignalP program (Nielsen et al., 1997, *Protein Engineering* 10: 1-6) that predicts amino acids 1 to 19 of SEQ ID NO: 2, amino acids 1 to 20 of SEQ ID NO: 4 and amino acids 1 to 19 of SEQ ID NO: 6 are signal peptides. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having lysozyme activity. In one aspect, the mature polypeptide coding sequence is the joint sequence of nucleotides 58 to 571 and nucleotides 639 to 859 of SEQ ID NO: 1, the joint sequence of nucleotides 61 to 267 and nucleotides 335 to 625 of SEQ ID NO: 3 or the joined sequence of nucleotides 58 to 133, nucleotides 215 to 345 and nucleotides 516 to 779 of SEQ ID NO: 5 based on the SignalP program (Nielsen et al., 1997, supra) that predicts nucleotides 1 to 57 of SEQ ID NO: 1, nucleotides 1 to 60 of SEQ ID NO: 3 and nucleotides 1 to 57 of SEQ ID NO: 5 encode signal peptides.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment−Total Number of Gaps in Alignment).

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having lysozyme activity. In one aspect, a subsequence contains at least 594 nucleotides (e.g., the joint sequence of nucleotides 175 to 571 and nucleotides 639 to 835 of SEQ ID NO: 1), or at least 690 nucleotides (e.g., the joint sequence of nucleotides 94 to 571 and nucleotides 639 to 850 of SEQ ID NO: 1). In another aspect, a subsequence contains at least 477 nucleotides (e.g., the joint sequence of nucleotides 73 to 267 and nucleotides 335 to 616 of SEQ ID NO: 3). In a further aspect, a subsequence contains at least 450 nucleotides (e.g., the joint sequence of nucleotides 70 to 133, nucleotides 215 to 345 and nucleotides 516 to 770 of SEQ ID NO: 5).

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having lysozyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position. A variant according to the invention may comprise from 1 to 5; from 1 to 10; from 1 to 15; from 1 to 20; from 1 to 52, i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 or 52 alterations.

DETAILED DESCRIPTION OF THE INVENTION

Polypeptides Having Lysozyme Activity

In an embodiment, the present invention relates to isolated polypeptides having a sequence identity to the mature polypeptide of SEQ ID NO: 2 of at least 80% which have lysozyme activity.

In an embodiment, the present invention relates to isolated polypeptides having a sequence identity to the mature polypeptide of SEQ ID NO: 2 of at least 85% which have lysozyme activity.

In an embodiment, the present invention relates to isolated polypeptides having a sequence identity to the mature polypeptide of SEQ ID NO: 2 of at least 90% which have lysozyme activity.

In an embodiment, the present invention relates to isolated polypeptides having a sequence identity to the mature polypeptide of SEQ ID NO: 2 of at least 91% which have lysozyme activity.

In an embodiment, the present invention relates to isolated polypeptides having a sequence identity to the mature polypeptide of SEQ ID NO: 2 of at least 92% which have lysozyme activity.

In an embodiment, the present invention relates to isolated polypeptides having a sequence identity to the mature polypeptide of SEQ ID NO: 2 of at least 93% which have lysozyme activity.

In an embodiment, the present invention relates to isolated polypeptides having a sequence identity to the mature polypeptide of SEQ ID NO: 2 of at least 94% which have lysozyme activity.

In an embodiment, the present invention relates to isolated polypeptides having a sequence identity to the mature polypeptide of SEQ ID NO: 2 of at least 95% which have lysozyme activity.

In an embodiment, the present invention relates to isolated polypeptides having a sequence identity to the mature polypeptide of SEQ ID NO: 2 of at least 96% which have lysozyme activity.

In an embodiment, the present invention relates to isolated polypeptides having a sequence identity to the mature polypeptide of SEQ ID NO: 2 of at least 97% which have lysozyme activity.

In an embodiment, the present invention relates to isolated polypeptides having a sequence identity to the mature polypeptide of SEQ ID NO: 2 of at least 98% which have lysozyme activity.

In an embodiment, the present invention relates to isolated polypeptides having a sequence identity to the mature polypeptide of SEQ ID NO: 2 of at least 99% which have lysozyme activity.

In one aspect, the polypeptides differ by no more than 52 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, from the mature polypeptide of SEQ ID NO: 2.

A polypeptide of the present invention preferably comprises or consists of the amino acid sequence of SEQ ID NO: 2 or an allelic variant thereof; or is a fragment thereof having lysozyme activity. In another aspect, the polypeptide comprises or consists of the mature polypeptide of SEQ ID NO: 2. In another aspect, the polypeptide comprises or consists of amino acids 20 to 264 of SEQ ID NO: 2.

In an embodiment, the present invention relates to isolated polypeptides having a sequence identity to the mature polypeptide of SEQ ID NO: 4 of at least 85% which have lysozyme activity.

In an embodiment, the present invention relates to isolated polypeptides having a sequence identity to the mature polypeptide of SEQ ID NO: 4 of at least 90% which have lysozyme activity.

In an embodiment, the present invention relates to isolated polypeptides having a sequence identity to the mature polypeptide of SEQ ID NO: 4 of at least 91% which have lysozyme activity.

In an embodiment, the present invention relates to isolated polypeptides having a sequence identity to the mature polypeptide of SEQ ID NO: 4 of at least 92% which have lysozyme activity.

In an embodiment, the present invention relates to isolated polypeptides having a sequence identity to the mature polypeptide of SEQ ID NO: 4 of at least 93% which have lysozyme activity.

In an embodiment, the present invention relates to isolated polypeptides having a sequence identity to the mature polypeptide of SEQ ID NO: 4 of at least 94% which have lysozyme activity.

In an embodiment, the present invention relates to isolated polypeptides having a sequence identity to the mature polypeptide of SEQ ID NO: 4 of at least 95% which have lysozyme activity.

In an embodiment, the present invention relates to isolated polypeptides having a sequence identity to the mature polypeptide of SEQ ID NO: 4 of at least 96% which have lysozyme activity.

In an embodiment, the present invention relates to isolated polypeptides having a sequence identity to the mature polypeptide of SEQ ID NO: 4 of at least 97% which have lysozyme activity.

In an embodiment, the present invention relates to isolated polypeptides having a sequence identity to the mature polypeptide of SEQ ID NO: 4 of at least 98% which have lysozyme activity.

In an embodiment, the present invention relates to isolated polypeptides having a sequence identity to the mature polypeptide of SEQ ID NO: 4 of at least 99% which have lysozyme activity.

In one aspect, the polypeptides differ by no more than 27 amino acids, e.g., 1, 2, 3, 4, 5, 6, 7, 8, 9, 10, 11, 12, 13, 14, 15, 16, 17, 18, 19, 20, 21, 22, 23, 24, 25 or 26, from the mature polypeptide of SEQ ID NO: 4.

A polypeptide of the present invention preferably comprises or consists of the amino acid sequence of SEQ ID NO: 4 or an allelic variant thereof; or is a fragment thereof having lysozyme activity. In another aspect, the polypeptide comprises or consists of the mature polypeptide of SEQ ID NO: 4. In another aspect, the polypeptide comprises or consists of amino acids 21 to 186 of SEQ ID NO: 4.

In an embodiment, the present invention relates to isolated polypeptides having a sequence identity to the mature polypeptide of SEQ ID NO: 6 of at least 90% which have lysozyme activity.

In an embodiment, the present invention relates to isolated polypeptides having a sequence identity to the mature polypeptide of SEQ ID NO: 6 of at least 91% which have lysozyme activity.

In an embodiment, the present invention relates to isolated polypeptides having a sequence identity to the mature polypeptide of SEQ ID NO: 6 of at least 92% which have lysozyme activity.

In an embodiment, the present invention relates to isolated polypeptides having a sequence identity to the mature polypeptide of SEQ ID NO: 6 of at least 93% which have lysozyme activity.

In an embodiment, the present invention relates to isolated polypeptides having a sequence identity to the mature polypeptide of SEQ ID NO: 6 of at least 94% which have lysozyme activity.

In an embodiment, the present invention relates to isolated polypeptides having a sequence identity to the mature polypeptide of SEQ ID NO: 6 of at least 95% which have lysozyme activity.

In an embodiment, the present invention relates to isolated polypeptides having a sequence identity to the mature polypeptide of SEQ ID NO: 6 of at least 96% which have lysozyme activity.

In an embodiment, the present invention relates to isolated polypeptides having a sequence identity to the mature polypeptide of SEQ ID NO: 6 of at least 97% which have lysozyme activity.

In an embodiment, the present invention relates to isolated polypeptides having a sequence identity to the mature polypeptide of SEQ ID NO: 6 of at least 98% which have lysozyme activity.

In an embodiment, the present invention relates to isolated polypeptides having a sequence identity to the mature polypeptide of SEQ ID NO: 6 of at least 99% which have lysozyme activity.

In one aspect, the polypeptides differ by no more than 17 amino acids, e.g., 1, 2, 3, 4, 5, 6, 7, 8, 9, 10, 11, 12, 13, 14, 15 or 16, from the mature polypeptide of SEQ ID NO: 6.

A polypeptide of the present invention preferably comprises or consists of the amino acid sequence of SEQ ID NO: 6 or an allelic variant thereof; or is a fragment thereof having lysozyme activity. In another aspect, the polypeptide comprises or consists of the mature polypeptide of SEQ ID NO: 6. In another aspect, the polypeptide comprises or consists of amino acids 20 to 176 of SEQ ID NO: 6.

In another embodiment, the present invention relates to an isolated polypeptide having lysozyme activity encoded by a polynucleotide that hybridizes under medium stringency conditions, medium-high stringency conditions, high stringency conditions, or very high stringency conditions with the mature polypeptide coding sequence of (i) SEQ ID NO: 1, SEQ ID NO: 3 or SEQ ID NO: 5, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1, SEQ ID NO: 3 or SEQ ID NO: 5 or a subsequence thereof, as well as the polypeptide of SEQ ID NO: 2, SEQ ID NO: 4 or SEQ ID NO: 6 or a fragment thereof, may be used to design nucleic acid probes to identify and clone DNA encoding polypeptides having lysozyme activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having lysozyme activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3 or SEQ ID NO: 5 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3 or SEQ ID NO: 5; (ii) the mature polypeptide coding sequence of SEQ ID NO: 1, SEQ ID NO: 3 or SEQ ID NO: 5; (iii) the cDNA sequence thereof (iv) the full-length complement thereof; or (v) a subsequence thereof; under medium to very high stringency conditions. Molecules to which the nucleic acid probe hybridizes under these conditions can be detected using, for example, X-ray film or any other detection means known in the art.

In one aspect, the nucleic acid probe is nucleotides 58 to 571 or nucleotides 639 to 859 of SEQ ID NO: 1, nucleotides 61 to 267 or nucleotides 335 to 625 of SEQ ID NO: 3, or nucleotides 58 to 133, nucleotides 215 to 345 or nucleotides 516 to 779 of SEQ ID NO: 5. In another aspect, the nucleic acid probe is a polynucleotide that encodes the polypeptide of SEQ ID NO: 2, SEQ ID NO: 4 or SEQ ID NO: 6; the mature polypeptide thereof; or a fragment thereof. In another aspect, the nucleic acid probe is SEQ ID NO: 1, SEQ ID NO: 3 or SEQ ID NO: 5 or the cDNA sequence thereof.

In another embodiment, the present invention relates to an isolated polypeptide having lysozyme activity encoded by a polynucleotide having a sequence identity to the mature polypeptide coding sequence of SEQ ID NO: 1 or the cDNA sequence thereof of at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to an isolated polypeptide having lysozyme activity encoded by a polynucleotide having a sequence identity to the mature polypeptide coding sequence of SEQ ID NO: 3 or the cDNA sequence thereof of at least 85%, at least 90%, at least 91%, at least 92%, at least 93%, at least 94%, at least 95%, at least 96%, at least 97%, at least 98%, at least 99%, or 100%.

In another embodiment, the present invention relates to an isolated polypeptide having lysozyme activity encoded by a polynucleotide having a sequence identity to the mature polypeptide coding sequence of SEQ ID NO: 5 or the cDNA sequence thereof of at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is not more than 52, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51.

In a further embodiment, the present invention relates to variants of the mature polypeptide of SEQ ID NO: 4 comprising a substitution, deletion, and/or insertion at one or more (e.g., several) positions. In an embodiment, the number of amino acid substitutions, deletions and/or insertions introduced into the mature polypeptide of SEQ ID NO: 4 is not more than 27, e.g., 1, 2, 3, 4, 5, 6, 7, 8, 9, 10, 11, 12, 13, 14, 15, 16, 17, 18, 19, 20, 21, 22, 23, 24, 25 or 26.

In an additional embodiment, the present invention relates to variants of the mature polypeptide of SEQ ID NO: 6 comprising a substitution, deletion, and/or insertion at one or more (e.g., several) positions. In an embodiment, the number of amino acid substitutions, deletions and/or insertions introduced into the mature polypeptide of SEQ ID NO: 6 is not more than 17, e.g., 1, 2, 3, 4, 5, 6, 7, 8, 9, 10, 11, 12, 13, 14, 15 or 16.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having Lysozyme Activity

A polypeptide having lysozyme activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a filamentous fungal polypeptide such as an *Acremonium*, *Aspergillus*, *Chrysosporium*, *Fusarium*, *Humicola*, *Penicillium*, *Thielavia* or *Trichoderma* polypeptide.

In another aspect, the polypeptide is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*,

*Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* polypeptide.

In another aspect, the polypeptide is an *Aspergillus aculeatus* or an *Acremonium alcalophilum* polypeptide, e.g., a polypeptide obtained from *Aspergillus aculeatus* CBS 172.66 or *Acremonium alcalophilum* CBS 114.92.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Aspergillus* or *Acremonium*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3 or SEQ ID NO: 5 or the cDNA sequences thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCI B 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMε1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Signal Peptide

The present invention also relates to an isolated polynucleotide encoding a signal peptide comprising or consisting of amino acids 1 to 19 of SEQ ID NO: 2, amino acids 1 to 20 or SEQ ID NO: 4 or amino acids 1 to 19 of SEQ ID NO: 6. The polynucleotides may further comprise a gene encoding a protein, which is operably linked to the signal peptide. The protein is preferably foreign to the signal peptide. In one aspect, the polynucleotide encoding the signal peptide is nucleotides 1 to 57 of SEQ ID NO: 1, nucleotides 1 to 60 of SEQ ID NO: 3 or nucleotides 1 to 57 of SEQ ID NO: 5.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will depend to a large extent upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991,

*Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M.I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is an *Aspergillus* or an *Acremonium* cell. In a more preferred aspect, the cell is an *Aspergillus aculeatus* or an *Acremonium alcalophilum* cell. In a most preferred aspect, the cell is *Aspergillus aculeatus* CBS 172.66 or *Acremonium alcalophilum* CBS 114.92.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides for example the lysozyme spot assay as described below. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germ plasma. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Uses

Examples of preferred uses of the lysozyme or compositions thereof of the present invention are given below. The dosage of the lysozyme and other conditions under which the lysozyme is used may be determined on the basis of methods known in the art.

The polypeptides of the invention are typically useful at any locus subject to contamination by bacteria, fungi, yeast or algae. Typically, loci are in aqueous systems such as cooling water systems, laundry rinse water, oil systems such as cutting oils, lubricants, oil fields and the like, where it is desired to kill the microorganisms or at least to control their growth. However, the present invention may also be used in all applications for which known lysozymes compositions are useful, such as protection of wood, latex, adhesive, glue, paper, cardboard, textile, leather, plastics, caulking, and feed.

A lysozyme, or a composition thereof, of the present invention may be used in several applications to degrade a material comprising a peptidoglycan or a chitodextrin by treating the material with the lysozyme or composition thereof (see for example Proctor and Cunningham, 1988, *Critical Reviews in Food Science and Nutrition* 26:359-395; Carini et al., 1985, *Microbiol. Alimen. Nutr.* 3:299-320; Hughey and Johnson, 1987, *Appl. Environ. Microbiol.* 53:2165-2170; Cunningham et al., 1991, *World's Poultry Science Journal* 47:141-163).

Uses of Lysozymes of the Invention for Cleaning and/or Detergents

A lysozyme of the present invention is preferably incorporated into and/or used together with detergent compositions as described below. When washing is performed repeatedly at temperatures below 60° C. there is an increased risk of malodour in the washing machine (laundry as well as dishwashing) and on the textiles or items washed in the machine. This malodour is likely to be caused by microbial organisms such as bacteria, fungi, algae or other unicellular organisms growing in the washing machine.

Furthermore, the invention relates to a process for laundering of fabrics comprising treating fabrics with a washing solution containing a detergent composition and a lysozyme or a lysozyme composition of the invention. The laundering treatment can for example be carried out in a machine washing process or in a manual washing process. The washing solution can for example be an aqueous washing solution containing the detergent composition and with a pH between 3 and 12.

The fabrics subjected to the methods of the present invention may be conventional washable laundry, for example household laundry. Preferably, the major part of the laundry is garments and fabrics, including knits, wovens, denims, yarns, and toweling, made from cotton, cotton blends or natural or manmade cellulosics (e.g., originating from wood pulp) or blends thereof. Examples of blends are blends of cotton or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax/linen, jute, cellulose acetate fibers, lyocell).

The present invention provides a method of reducing microbial contamination on a surface, such as a textile garment or hard surface such as metal, plastic or rubber parts in a washing machine or dish washing machine, bathroom tiles, floors, table tops, drains, sinks and washbasin, by treating the microbially contaminated surface with a lysozyme or lysozyme composition of the present invention.

Such a treatment is also expected to reduce the malodour on textiles and hard surfaces containing microbial contamination.

The reduction of microbial contamination can be assessed in several ways, for example by letting a panel assess whether the smell has been decreased, alternatively a sample may be taken from the surface and cultivated to assess whether the microbial count has been reduced as a result of the treatment compared to a treatment without lysozyme.

Uses of Lysozymes of the Invention in Animal Feed

A lysozyme of the invention may also be used in animal feed. In an embodiment, the present invention provides a method for preparing an animal feed composition comprising adding a lysozyme of the present invention to one or more animal feed ingredients.

A lysozyme of the present invention may for example be used to stabilize the healthy microflora of animals, in particular livestock such as, but not limited to, sheep, goats, cattle (including, but not limited to, beef cattle, cows, and young calves), deer, pigs or swine (including, but not limited to, piglets, growing pigs, and sows), poultry (including, but not limited to, geese, turkeys, ducks and chicken such as broilers, chicks and layers); horses, moose and rabbits but also in fish (including but not limited to salmon, trout, tilapia, catfish and carps; and crustaceans (including but not limited to shrimps and prawns)). In a preferred embodiment, the lysozyme replaces antibiotics in animal diets. In a further embodiment, a lysozyme of the present invention is used as a feed additive, where it may provide a positive effect on the microbial balance of the chicken digestive tract and in this way improve animal performance.

A lysozyme of the present invention may also be used in animal feed as feed enhancing enzymes that improve feed digestibility to increase the efficiency of its utilization according to WO 00/21381 and WO 2004/026334.

In a further embodiment, a lysozyme of the present invention may be used as a feed additive, where it may provide a positive effect on the animals digestive tract and in this way improve animal performance in accordance to weight gain, feed conversion ratio (FCR), or improved animal health such as decreased mortality rate. FCR is calculated as the feed intake in g/animal relative to the weight gain in g/animal.

Uses of Lysozymes of the Invention as Antimicrobial Agents

A lysozyme of the present invention may be used as antimicrobial agents. One aspect of the present invention is a method for reducing microbial contamination, comprising treating a microbial contaminated surface with a lysozyme of the present invention.

To assess whether a lysozyme of the present invention is capable of acting as an antimicrobial agent it can be tested in a turbidity assay. In this assay it is tested whether the lysozyme is capable of degrading microbial cells, e.g., a dried substrate of *Exiguobacterium undae* cells (isolated from a smelly sock) or *Micrococcus luteus* cells dissolved in buffer or detergent, and thereby reducing the optical density (OD) at for example 540 nm, when compared to a microbial suspension only treated with buffer.

Uses of Lysozymes of the Invention for Disinfection or as a Disinfectant

A lysozyme of the present invention may be useful as a disinfectant or used for disinfection, e.g., for the treatment of infections in the eye or the mouth, or for cleaning and disinfection of contact lenses, and for preventing or removing biofilm on a surface according to U.S. Pat. No. 6,777,223.

A lysozyme of the present invention may also be used in oral care. For example, lysozyme can be used alone or in combination with other enzymes or even antimicrobial peptides in toothpaste or other oral care products. The polypeptides may be introduced into the oral cavity or applied to an article that is to be introduced into the oral cavity. See for example WO 2008/124764.

In general it is contemplated that the polypeptides of the present invention are useful for cleaning, disinfecting or inhibiting microbial growth on any surface. Examples of surfaces, which may advantageously be contacted with the polypeptides of the invention are surfaces of process equipment used, e.g., dairies, chemical or pharmaceutical process plants, water sanitation systems, oil processing plants, paper pulp processing plants, water treatment plants, and cooling towers. The polypeptides of the invention should be used in an amount, which is effective for cleaning, disinfecting or inhibiting microbial growth on the surface in question.

The polypeptides of the invention may additionally be used for cleaning surfaces and cooking utensils in food processing plants and in any area in which food is prepared or served such as hospitals, nursing homes and restaurants.

Uses of Lysozymes of the Invention in Food Applications

A lysozyme of the present invention may also be used to selectively inhibit the uncontrolled growth of *Clostridium tyrobutyricum* during the maturation of cheeses, in particular, those made from pressed and cooked curds, e.g., Swiss Cheese, Parmesan, Edam, Gouda, Cheddar, and many others.

A lysozyme of the present invention may also be used in wine making, to control or inhibit microbial contamination.

Uses of Lysozymes of the Invention as Treatments

A lysozyme of the present invention may also be used in topical treatment of dystrophic and inflammatory lesions of the skin and soft tissues. See, e.g., Palmieri and Boraldi, 1977, *Arch. Sci. Med.* (Torino) 134:481-485.

A lysozyme of the present invention may also be used in skin care. For example, the polypeptide is applied to the skin of a patient suffering from a skin infection, such as acne. The lysozyme may also be used in a wound dressing, which is applied to wounded skin, for example, to aid in healing of the wound. See, for example, U.S. Application No. 2008/0254079.

A lysozyme of the present invention may also be used in lipstick, lip balm, lip gel, or lip gloss. For example, such products can be used for treatment of a localized lip infection, for example, a cold sore. See, for example, U.S. Application No. 2008/0254079.

A lysozyme of the present invention may also be used in the treatment of bronchopulmonary diseases.

A lysozyme of the present invention may also be used as digestive enzymes or digestive aids. A lysozyme of the present invention may also be used to improve the use of dead/live bacteria as a food source, e.g., by controlling undesirable microbial contaminants.

A lysozyme of the present invention may also be used as a therapeutic in a human or other animal, e.g., to control or inhibit bacterial overgrowth in the intestines of a human suffering from a disease, e.g., pancreatic disease or an immuno compromised patient.

Uses of Lysozymes of the Invention for Extracting Bacterial Genomic DNA

A lysozyme of the present invention may also be used to aid in the extraction of bacterial genomic DNA. In order to be able to sequence bacterial DNA, the bacterial cell wall needs to be broken down to isolate the DNA inside it. The cell wall of especially gram positive bacteria can be difficult to break down.

Hen egg white lysozyme is the standard enzyme used for DNA isolation from gram positive bacteria and works by hydrolyzing the peptidoglycan chains present in the cell wall thereby aiding in the degradation of the cell walls. However some gram positive cell walls are not degraded by hen egg white lysozymes. For example, it is recommended that cells from, e.g., *Staphylococcus aureus* are lysed with lysostaphin as described by Pitcher and Saunders, 1989, *App. Environ. Microbiol.* 56(3): 782-787. However, these methods do not work for all types of gram positive bacteria and novel lysozymes thus potentially offer access to novel genomes that cannot be isolated with commercial lysozyme solutions.

Other Uses of Lysozymes of the Invention

A lysozyme of the present invention may also be used to control microbial growth in a fermentation process, such as, in making ethanol or other products from biomass. See, e.g., WO 2007/109750. Accordingly, the lysozyme may be used, e.g., in a process for producing a fermentation product comprising (a) liquefying and/or saccharifying a carbohydrate material and (b) fermenting using a fermentation organism, wherein a lysozyme of the present invention is applied to the fermentation process before, during and/or after fermentation concentrations sufficient to kill and/or inhibit growth of bacterial cells.

A lysozyme of the present invention may also be used in controlling microbial growth in a fish or shrimp farm.

Other uses include preservation of foods, beverages, cosmetics such as lotions, creams, gels, ointments, soaps, shampoos, conditioners, antiperspirants, deodorants, enzyme formulations, or food ingredients.

Compositions

In a still further aspect, the present invention relates to compositions comprising a polypeptide of the present invention having antimicrobial and/or lysozyme activity.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Animal Feed Compositions

The present invention is also directed to methods for using the polypeptides of the present invention having lysozyme activity in animal feed, as well as to feed compositions and feed additives comprising the lysozymes of the invention.

The term animal includes all animals, including human beings. Examples of animals are non-ruminants, and ruminants. Ruminant animals include, for example, animals such as sheep, goats, and cattle, e.g., beef cattle and cows. In a particular embodiment, the animal is a non-ruminant animal. Non-ruminant animals include mono-gastric animals, e.g., pigs or swine (including, but not limited to, piglets, growing pigs, and sows); poultry such as turkeys, geese, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal. In the use according to the invention the lysozyme can be fed to the animal before, after, or simultaneously with the diet. The latter is preferred. Such lysozyme compositions may of course be mixed with other enzymes.

The lysozyme can be added to the feed in any form, be it as a relatively pure lysozyme or in admixture with other components intended for addition to animal feed, i.e., in the form of animal feed additives, such as the so-called pre-mixes for animal feed. In a further aspect, the present invention relates to compositions for use in animal feed, such as animal feed, and animal feed additives, e.g., pre-mixes.

Apart from the lysozyme of the invention, the animal feed additives of the invention contain at least one fat-soluble vitamin, and/or at least one water soluble vitamin, and/or at least one trace mineral, and/or at least one macro mineral.

Further, optional, feed-additive ingredients are colouring agents, e.g., carotenoids such as beta-carotene, astaxanthin, and lutein; stabilisers; growth improving additives and aroma compounds/flavorings, e.g., creosol, anethol, deca-, undeca- and/or dodeca-lactones, ionones, irone, gingerol, piperidine, propylidene phthalide, butylidene phatalide, capsaicin and/or tannin; polyunsaturated fatty acids (PUFAs); reactive oxygen generating species; also, a support may be used that may contain, for example, 40-50% by weight of wood fibres, 8-10% by weight of stearine, 4-5% by weight of *curcuma* powder, 4-58% by weight of rosemary powder, 22-28% by weight of limestone, 1-3% by weight of a gum, such as gum arabic, 5-50% by weight of sugar and/or starch and 5-15% by weight of water.

A feed or a feed additive of the invention may also comprise at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usally fat- and water-soluble vitamins, as well as trace minerals form part of a so-called premix intended for addition to the feed, whereas macro minerals are usually separately added to the feed. Either of these composition types, when enriched with a protease of the invention, is an animal feed additive of the invention.

In a particular embodiment, the animal feed additive of the invention is intended for being included (or prescribed as having to be included) in animal diets or animal feed at levels of 0.1 ppm to 1000 ppm, preferably 0.5 ppm to 200 ppm and more preferably 1 ppm to 100 ppm. The aforementioned dosing levels can also be used for premixes.

The animal feed composition of the invention may contain at least one vegetable protein, such as that derived from or originating from a vegetable, including modified proteins and protein-derivatives. Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal, Alternatively, the vegetable protein source is material from one or more plants of the family Chenopodiaceae, e.g., beet, sugar beet, spinach or *quinoa*. Other examples of vegetable protein sources are rapeseed, sunflower seed, cotton seed, and cabbage and cereals such as barley, wheat, rye, oat, maize (corn), rice, triticale, and sorghum.

The animal feed composition of the invention may also contain animal protein, such as Meat and Bone Meal, Feather meal, and/or Fish Meal, typically in an amount of 0-25%. The animal feed composition of the invention may also comprise Dried Destillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can, e.g., be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) lysozyme/enzyme preparation may also be added before or during the feed ingredient step. Typically a liquid lysozyme/enzyme preparation is added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

Cleaning or Detergent Compositions

The lysozyme of the invention may be added to and thus become a component of a detergent composition, particularly in a liquid detergent having a pH of 7 or lower.

The detergent composition of the invention may for example be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the lysozyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

In one embodiment, the invention is directed to cleaning or detergent compositions comprising of an enzyme of the present invention in combination with one or more additional cleaning components. The choice of additional cleaning components is within the skill of the artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although the components mentioned below are categorized according to a particular function, this should not be construed as a limitation since the component may have one or more additional functionalities which the skilled artisan will appreciate.

The cleaning or detergent composition may be suitable for the laundring of textiles such as, e.g., fabrics, cloths or linen, or for cleaning hard surfaces such as, e.g., floors, tables, or dish wash.

The invention also relates to polynucleotides encoding the polypeptides, nucleic acid constructs, vectors, and host cells comprising the polynucleotides as well as methods of producing and using the polypeptides.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 0% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0% to about 10% by weight of a semipolar surfactant. Non-limiting examples of semipolar surfactants include amine oxides (AO) such as alkyldimethylamineoxide, N—(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 0% to about 10% by weight of a zwitterionic surfactant. Non-limiting examples of zwitterionic surfactants include betaine, alkyldimethylbetaine, sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however, the molecular structure of hydrotropes generally do not favor spontaneous self-aggregation, see, e.g., review by Hodgdon and Kaler, 2007, *Current Opinion in Colloid & Interface Science* 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 45% of a detergent builder or co-builder, or a mixture thereof. In a dish wash deteregent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-20% by weight, such as about 5% to about 10%, of a detergent co-builder, or a mixture thereof. The detergent composition may include include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra-(methylenephosphonic acid) (EDTMPA), diethylenetriaminepentakis(methylenephosphonic acid) (DTPMPA or DTMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N, N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)-ethylidenediamine-N,N', N'-triacetate (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 2009/102854, U.S. Pat. No. 5,977,053.

Bleaching Systems

The detergent may contain 0-50% by weight, such as about 0.1% to about 25%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone®, and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetraacetylethylene diamine (TAED), sodium 4-[(3,5,5-trimethylhexanoyl)oxy]benzene sulfonate (ISONOBS), diperoxy dodecanoic acid, 4-(dodecanoyloxy) benzenesulfonate (LOBS), 4-(decanoyloxy)benzenesulfonate, 4-(decanoyloxy)benzoate (DOBS), 4-(nonanoyloxy)—benzenesulfonate (NOBS), and/or those disclosed in WO 98/17767. A particular family of bleach activators of interest was disclosed in EP 624154 and particularly preferred in that family is acetyl triethyl citrate (ATC). ATC or a short chain triglyceride like triacetin has the advantage that it is environmental friendly as it eventually degrades into citric acid and alcohol. Furthermore, acetyl triethyl citrate and triacetin has a good hydrolytical stability in the product upon storage and it is an efficient bleach activator. Finally, ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments, the bleach component may be an organic catalyst selected from the group consisting of organic catalysts having the following formulae:

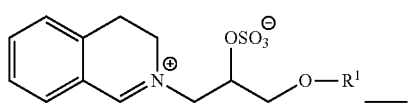
(i)

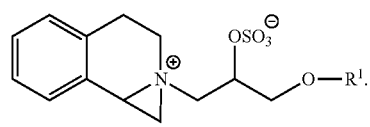
(ii)

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO 2007/087258, WO 2007/087244, WO 2007/087259 and WO 2007/087242. Suitable photobleaches may for example be sulfonated zinc phthalocyanine.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt. % to about 0.2 wt. %, from about 0.00008 wt. % to about 0.05 wt. %, or even from about 0.0001 wt. % to about 0.04 wt. % fabric hueing agent. The composition may comprise from 0.0001 wt % to 0.2 wt. % fabric hueing agent, this may be especially preferred when the composition is in the form of a unit dose pouch. Suitable hueing agents are also disclosed in, e.g., WO 2007/087257 and WO 2007/087243.

Additional Enzymes

In one aspect, the present invention provides a detergent additive comprising a lysozyme of the present invention. The detergent additive as well as the detergent composition may comprise one or more [additional] enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583. Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase™, Savinase™ Primase™, Duralase™, Esperase™, and Kannase™ (Novozymes A/S), Maxatase™, Maxacal™ Maxapem™, Properase™, Purafect™, Purafect OxP™, FN2™, and FN3™ (Genencor International Inc.).

Lipases and Cutinases: Suitable lipases and cutinases include those of bacterial or fungal origin. Chemically modified or protein engineered mutant enzymes are included. Examples include lipase from *Thermomyces*, e.g., from T. *lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), P. sp. strain SD705 (WO 95/06720 & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/87508 and WO 2009/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/56782), perhydrolases from the CE 7 family (WO 2009/67279), and variants of the *M. smegmatis* perhydrolase in particular the S54V variant used in the commercial product Gentle Power Bleach from Huntsman Textile Effects Pte Ltd (WO 2010/100028).

Amylases: Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™, Stainzyme™ Natalase™ and BAN™ (Novozymes A/S), Rapidase™ and Purastar™ (from Genencor International Inc.).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants:

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents:

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent:

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2.2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-naptho-1,2':4,5)—1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt. % to upper levels of 0.5 or even 0.75 wt. %.

Soil Release Polymers:

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents:

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Biofilms

Microorganisms growing in biofilms are less susceptible to all types of antimicrobial agents than the same microorganisms when grown in conventional suspension cultures.

It is well known that starved bacteria can be much less susceptible to a variety of antimicrobial challenges. For example, a number of classical antibiotics such as penicillin, perform poorly in slow or non dividing bacteria. Because lysozyme attacks and destroys the peptidoglycan layer regardless of the growth state of the bacteria, it remains effective.

Biofilm Control; Example Dental Water Lines:

Biofilm buildup within a dental water line can contain biofilms consisting of *Pseudomonas aeruginosa, Proteus mirabilis, Legionella* sp. to name but a few. There is also the possibility of colonisation of species generally found within the oral cavity as a result of the failure of anti retraction valves within the system. The risk of cross infection becomes even more of a potential risk of course when immuno—compromised patients are involved and in this day and age the numbers of patients within this category continues to steadily increase. The need exists for effective control of bacterial biofilm accumulation in dental water lines. A review of biofilms can be found: Watnick and Kolter, 2000, "Biofilm, city of microbes", *J. Bacteriol.* 182(10):2675-2679.

A typical example of a commercial throat lozenge product is Lysopaine produced by: Boehringer Ingelheim (France)

Active ingredients:

BACITRACIN 200 U.I.
(to 65 iu/mg)
PAPAIN 2 mg
to 30 NK/mg
LYSOZYME CHLORHYDRATE 5 mg
to 26000 U FIP/mg: units determined by measuring OD kinetics of lysis of bacteria suspended in buffer. The unit determination was measured by lysis induced change in turbidity of a bacterial culture suspended in buffer.

Non active ingredients:

SACCHARIN excipient
MAGNESIUM STEARATE excipient
Menthol aromatisant
SORBITOL excipient For local treatment of point infections limited to the buccal membranes of the oropharynx. Caution, if clinical indications of a general bacterial infection are evident, antibiotic therapy is advised.

Toothpaste:

Lysozyme can be used alone or in combination with other enzymes or even antimicrobial peptides. Examples of other enzymes are glucose oxidase and lactoperoxidase.

A typical toothpaste composition including lysozyme is "Biotene" by Laclede, Inc., 2030 East University Drive, Rancho Domiguez, Calif. 90220, USA.

Active Ingredients

Contains: Lactoperoxidase (100 gm)

Inactive Ingredients

Glucose Oxidase, Lysozyme, Sodium Monofluorophosphate, Sorbitol, Glycerin, Calcium Pyrophosphate, Hydrated Silica, Zylitol, Cellulose Gum, Flavor, Sodium Benzoate, Beta-d-glucose, Potassium Thiocyanate The present invention is further described by the following examples that should not be construed as limiting the scope of the invention.

EXAMPLES

Strains

*Aspergillus aculeatus* CBS 172.66 was used as the source of DNA for obtaining the coding region encoding the GH23 lysozyme candidate. According to Central Bureau vor Schnimmelkulture, *Aspergillus aculeatus* CBS 172.66 was isolated by K. B. Raper in 1962 from tropical soil.

*Aspergillus oryzae* MT3568 strain was used for expression of the *A. aculeatus* gene encoding the enzyme. *A. oryzae* MT3568 is an amdS (acetamidase) disrupted gene derivative of *Aspergillus oryzae* JaL355 (WO 02/40694) in which pyrG auxotrophy was restored by disrupting the *A. oryzae* acetamidase (amdS) gene with the pyrG gene.

According to Central Bureau vor Schnimmelkulture, *Acremonium alkalophilum* CBS 114.92 was isolated by A. Yoneda in 1984 from the sludge of pig faeces compost near Tsukui Lake, Japan.

Media and Solutions

YP medium was composed of 10 g of yeast extract, 20 g of Bactopeptone, and deionized water to 1 liter.

LB medium was composed of 10 g of tryptone, 5 g of yeast extract, 5 g of sodium chloride, and deionized water to 1 liter.

Horikoshi agar medium was composed of: 1% (w/v) Dextrose, 1% soluble starch, 0.5% (w/v) peptone, 0.5% (w/v) yeast extract, 0.02% (w/v) $MgSO_4.7H_2O$, 0.1% (w/v) $K_2HPO_4$, and 15 g (w/v) of Bacto-agar. 1% (w/v) $Na_2CO_3$ was added separately after sterilization.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g (w/v) of dextrose and 20 g (w/v) of agar powder. The medium was sterilized by autoclaving at 15 psi for 15 minutes (Bacteriological Analytical Manual, 8th Edition, Revision A, 1998).

COVE sucrose plates were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl and Triton X-100 (50 µl/500 ml) were added.

LB agar plates were composed of 37 g of LB agar and deionized water to 1 liter.

COVE salt solution was composed of 26 g of $MgSO_4.7H_2O$, 26 g of KCL, 26 g of $KH_2PO_4$, 50 ml of COVE trace metal solution, and deionized water to 1 liter.

COVE trace metal solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

Dap-4C medium was composed of 20 g of dextrose, 10 g of maltose, 11 g of $MgSO_4.7H_2O$, 1 g of $KH_2PO_4$, 2 g of citric acid, 5.2 g of $K_3PO_4.H_2O$, 0.5 g of yeast extract (Difco), 1 ml of antifoam, 0.5 ml KU6 trace metals solution, 2.5 g of $CaCO_3$, and deionized water to 1 liter. The medium was sterilized by autoclaving at 15 psi for 15 minutes (Bacteriological Analytical Manual, 8th Edition, Revision A, 1998). Before use, 3.5 ml of sterile 50% $(NH_4)_2HPO_4$ and 5 ml of sterile 20% lactic acid were added per 150 ml of medium.

YP+2% glucose medium was composed of 1% yeast extract, 2% peptone and 2% glucose.

Example 1: Lysozyme Assay

*Xanthomonas campestris* is the production organism for all xanthan gum production. The separation of *Xanthomonas* cells from the highly viscous xanthan solution is a cost-intensive process in the industrial production (Homma et al., EP 690072, Murofushi et al., EP 718311, U.S. Pat. No. 5,702,927). Nowadays, the favoured method for recovering xanthan from the fermentation liquid is precipitation with alcohol, mainly isopropanol, after pasteurization to destroy bacterial cells and enzymes (Cottrell et al., 1978, "Xanthan gum: A unique bacterial polysaccharide for food applications", *Ind. Microbiol*, 19:177). Subsequently the xanthan/cell debris precipitate is spray dried and milled to a powder. The alcohol is recovered by distillation. Because of the significant amounts of *Xanthomonas* cell wall debris in some commercial preparations of xanthan gum, and this debris is peptidoglycan rich *Xanthomonas* cell wall material, the gum can be used as a convenient assay for peptidoglycan degrading activity.

Solid Plate Assay:

Commercially prepared Xanthan gum (Sigma # G-1253) is dissolved in a buffered solution or bacterial growth media to 0.5% w/v in the presence of 0.7% agarose and then autoclaved. Enzyme preparations, supernatants or whole organisms are either deposited in wells cut out of the Bacto agar plates or deposited directly on the surface of the media. The preparations are able to form clearing zones in the plates. These clearing zones can indicate degradation of bacterial cell wall material.

Liquid Clearing Assay:

Commercially prepared xanthan gum is dissolved in a buffered solution in the presence or absence of sodium chloride. The solution is autoclaved and used for studies of xanthan gum clearing. Enzyme preparations, supernatants or whole organisms are added to the assay medium and incubated. Resulting treatments are measured in a spectrophotometer to determine the OD of the solution. Typically, a wavelength of 600 nm is used.

Example 2: Cloning and Characterization of the *Aspergillus aculeatus* GH23 Lysozyme (SEQ ID NO: 2)

Genomic sequence information was generated by the U.S. Department of Energy Joint Genome Institute (JGI). According to Central Bureau vor Schnimmelkulture, *Aspergillus aculeatus* CBS 172.66 was isolated by K. B. Raper in 1962 from tropical soil. A preliminary assembly of the genome was downloaded from JGI and analyzed using the Pedant-Pro™ Sequence Analysis Suite (Biomax Informatics AG, Martinsried, Germany). Gene models constructed by the software were used as a starting point for detecting GH23 homologues in the genome. More precise gene models were constructed manually using multiple known GH23 protein sequences as a guide.

To generate genomic DNA for PCR amplification, *Aspergillus aculeatus* CBS 172.66 was propagated on PDA agar plates by growing at 26° C. for 7 days. Spores harvested from the PDA plates were used to inoculate 25 ml of YP+2% glucose medium in a baffled shake flask and incubated at 26° C. for 48 hours with agitation at 200 rpm.

Genomic DNA was isolated according to a modified FastDNA® SPIN protocol (Qbiogene, Inc., Carlsbad, Calif., USA). Briefly a FastDNA® SPIN Kit for Soil (Qbiogene, Inc., Carlsbad, Calif., USA) was used in a FastPrep® 24 Homogenization System (MP Biosciences, Santa Ana, Calif., USA). Two ml of fungal material from the above cultures were harvested by centrifugation at 14,000×g for 2 minutes. The supernatant was removed and the pellet resuspended in 500 µl of deionized water. The suspension was transferred to a Lysing Matrix E FastPrep® tube (Qbiogene, Inc., Carlsbad, Calif., USA) and 790 µl of sodium phosphate buffer and 100 µl of MT buffer from the FastDNA® SPIN Kit were added to the tube. The sample was then secured in the FastPrep® Instrument (Qbiogene, Inc., Carlsbad, Calif., USA) and processed for 60 seconds at a speed of 5.5 m/sec. The sample was then centrifuged at 14000×g for two minutes and the supernatant transferred to a clean EPPENDORF® tube. A 250 µl volume of PPS reagent from the FastDNA® SPIN Kit was added and then the sample was mixed gently by inversion. The sample was again centrifuged at 14000×g for 5 minutes. The supernatant was transferred to a 15 ml tube followed by 1 ml of Binding Matrix suspension from the FastDNA® SPIN Kit and then mixed by inversion for two minutes. The sample was placed in a stationary tube rack and the silica matrix was allowed to settle for 3 minutes. A 500 µl volume of the supernatant was removed and discarded and then the remaining sample was resuspended in the matrix. The sample was then transferred to a SPIN filter tube from the FastDNA® SPIN Kit and centrifuged at 14000×g for 1 minute. The catch tube was emptied and the remaining matrix suspension added to the SPIN filter tube. The sample was again centrifuged (14000×g, 1 minute). A 500 µl volume of SEWS-M solution from the FastDNA® SPIN Kit was added to the SPIN filter tube and the sample was centrifuged at the same speed for 1 minute. The catch tube was emptied and the SPIN filter replaced in the catch tube. The unit was centrifuged at 14000×g for 2 minutes to "dry" the matrix of residual SEWS-M wash solution. The SPIN filter was placed in a fresh catch tube and allowed to air dry for 5 minutes at room temperature. The matrix was gently resuspended in 100 µl of DES (DNase/Pyrogen free water) with a pipette tip. The unit was centrifuged (14000×g, 1 minute) to elute the genomic DNA followed by elution with 100 µl of 10 mM Tris, 0.1 mM EDTA, pH 8.0 by renewed centrifugation at 14000×g for 1 minute and the eluates were combined. The concentration of the DNA harvested from the catch tube was measured by a UV spectrophotometer at 260 nm.

Construction of an *Asperqillus oryzae* Expression Vector Containing *Asperqillus aculeatus* CBS 172.66 Genomic Sequence Encoding a Family GH23 Polypeptide P24DZF Having Lysozyme Activity.

Two synthetic oligonucleotide primers shown in table 1 below were designed to PCR amplify the *Aspergillus aculeatus* CBS 172.66 P8EH GH23 gene from the genomic DNA. An IN-FUSION™ Cloning Kit (Clontech, Mountain View, Calif., USA) was used to clone the fragment directly into the expression vector pDau109 (WO 2005/042735).

TABLE 1

Primers used for GH23 PCR Amplification

| GH23 gene | Specific forward primer | Specific reverse primer |
|---|---|---|
| Aspergillus aculeatus CBS 172.66 | F-P8EH 5'-ACACAACTGGGG ATCCACCATGCAGTT GAACAACTTCCTTC T-3' (SEQ ID NO: 9) | R-P8EH 5'-AGATCTCGAGAA GCTTACTATGCGCTC AGGGTGCACT-3' (SEQ ID NO: 10) |

Bold letters represent coding sequence. The underlined sequence is homologous to the insertion sites of pDau109.

The PCR reaction (25 µl) was composed of 12.5 µl of 2×IPROOF™ HF Master Mix, 0.5 µl of primer F-P24DZF (100 µM), 0.5 µl of primer R-P24DZF (100 µM), 0.5 µl of genomic (100 ng/µl), and 11 µl of deionized water. The PCR reaction was incubated in a DYAD® Dual-Block Thermal Cycler (MJ Research Inc., Waltham, Mass., USA) programmed for 1 cycle at 98° C. for 30 seconds; 30 cycles each at 98° C. for 10 seconds, 55° C. for 10 seconds, and 72° C. for 60 seconds; and 1 cycle at 72° C. for 10 minutes. Samples were cooled to 10° C. before removal and further processing.

Five µl of the PCR reaction were analyzed by 1% agarose gel electrophoresis using TAE buffer where an approximately 770 bp product band was observed. The remaining PCR reaction was purified using an ILLUSTRA™ GFX™ PCR DNA and Gel Band Purification Kit according to the manufacturer's instructions.

The fragment was then cloned into Hind III and Bam HI digested pDau109 using an IN-FUSION™ Cloning Kit resulting in plasmid pP8EH. Cloning of the P24DZF gene into Hind III-Bam HI digested pDau109 resulted in the transcription of the *Aspergillus aculeatus* P24DZF gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The cloning protocol was performed according to the IN-FUSION™ Cloning Kit instructions generating a P24DZF GH23 construct. The treated plasmid and insert were transformed into Fusion Blue™ *E. coli* cells (Clontech, Mountain View, Calif., USA) according to the manufacturer's protocol and plated onto LB plates supplemented with 50 µg of ampicillin per ml. After incubating at 37° C. overnight, colonies were seen growing under selection on the LB ampicillin plates. Ten colonies transformed with the P24DZF GH23 construct were cultivated in LB medium supplemented with 50 µg of ampicillin per ml and plasmid was isolated using a FASTPlasmid mini kit from 5Prime (5 PRIME GmbH, Königstrasse 4a, 22767 Hamburg, Germany) according to the manufacturer's instructions.

Isolated plasmids were sequenced with vector primers and in order to determine a representative plasmid expression clone that was free of PCR errors.

Characterization of the Asperqillus *Aculeatus* CBS 172.66 Genomic Sequences Encoding GH23 Polypeptide DNA sequencing of the *Aspergillus aculeatus* CBS172.66 P24DZF GH23 genomic clone was performed with an Applied Biosystems Model 3730xl Automated DNA Sequencer using version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA). The sequence obtained was identical to the sequence from the JGI and is shown in SEQ ID NO: 1.

The nucleotide sequence and deduced amino acid sequence of the *Aspergillus aculeatus* P24DZF GH23 gene are shown in SEQ ID NO: 1 and SEQ ID NO: 2, respectively. The coding sequence is 862 bp including the stop codon and is interrupted by a single intron of 67 bp (nucleotides 572 to 638). The encoded predicted protein is 264 amino acids and is shown in SEQ ID NO: 2. Using the SignalP program (Nielsen et al., 1997, *Protein Engineering* 10: 1-6), a signal peptide of 19 residues was predicted. The predicted mature protein contains 245 amino acids.

The *Aspergillus oryzae* strain MT3568 was used for all experiments. *Aspergillus oryzae* MT3568 is an amdS (acetamidase) disrupted derivative of *A. oryzae* JaL355 (WO 02/40694) in which pyrG auxotrophy was restored in the process of knocking out the *A. oryzae* amdS gene. *A. oryzae* MT3568 protoplasts were prepared according to the method of European Patent, EP 0238023, pages 14-15. Fresh protoplasts of *A. oryzae* MT3568 were prepared and transformed with the P24DZF GH23 plasmid. Plasmid DNA from the above mini prep procedure was used to transform *A. oryzae* MT3568.

Six ul containing about 3.0 µg total DNA was used for the transformation. The DNA was gently added to 100 µl of *A. oryzae* MT3568 protoplasts and 250 µl of 60% PEG 4000 (Sigma-Aldrich cat. No. 95904). The 60% (W/V) PEG 4000 was prepared in the following manner: PEG 4000 powder was dissolved in double distilled $H_2O$ and then heated for 10-20 seconds in a microwave oven at 800 watt until dissolved. The dissolved solution was cooled down to room temperature and then then adjusted with $CaCl_2$ solution and Tris-HCl solution (pH 7.5) for a final concentration of 10 mM of each. After adding the 60% PEG 4000 solution, the tube was gently mixed and incubated at 37° C. for 30 minutes. The mix was added to 6 ml of top agar with 10 mM acetamide and plated onto COVE-sorbitol plates with 10 mM acetamide.

The plates were incubated at 37° C. for 3 or more days and then moved to 26° C. for two days. Spores from 8 individual colonies were picked by first dipping a white 10 µl inoculation pin (Nunc A/S, Denmark) in a 0.1% TWEEN® 80 solution, contacting the sporulating colony on the selection plate, and restreaking with the pin onto fresh COVE sorbitol plates containing 10 mM acetamide. After 5 days at 26° C., spores from the restreaked colonies were used to inoculate a 96 well deep dish plate (NUNC, cat. no. 260251, Thermoscientific, USA). The wells of the deep dish plate contained 500 uls of either YP+2% glucose or DAP4C media. The inoculated plate was sealed with gas permeable tape (89009-656, VWR.com). Plates were incubated stationary at 30 C for 5 days. Expression was verified by analysis of 20 uls of harvested culture fluid on SDS-PAGE using a NUPAGE® 10% Bis-Tris gel (Invitrogen, Carlsbad, Calif., USA) and Coomassie blue staining. One transformant was selected for further work and designated *A. oryzae* EXP03899.

Spores of EXP03899 were inoculated into both YP+2% glucose medium and DAP-4C-1 medium (100 mls in 500 ml Erlenmeyer shake flask with baffles). The cultures were incubated at 26° C. and 150 rpm, 3 days and if necessary 4 days. An SDS gel was run as above to test protein amount.

Plate Test for Lysozyme Activity

A Spot assay was performed with Xanthan gum, at pH 5, 7 and 8 as described in the section lysozyme plate assay.

A 1.5% Agarose (Invitrogen cat. 15510-027, electrophoresis grade) solution was prepared in the following buffers:
pH ~5—in water
pH ~7—in 0.02M potassium phosphate pH 7
pH ~8—in 0.02M potassium phosphate pH 8

The agarose was autoclaved for 20 minutes at 121° C. 0.5% Xanthan gum (Sigma G1253) was dissolved in the melted 1.5% agarose and the mixture poured into petri plates. When the plates were set, sample application wells were made with a P-1000 pippette tip (cut off to a 3 mm diameter) attached to a vacuum line.

20 ul of the culture fluid of EXP03899 was deposited in the application wells and incubated at 37° C. over night. Samples with lysozyme activity were observed by clearing zones where the cell debris in the xanthan gum was observed. Culture fluids from EXP03899 displayed such a clearing zone while the *Aspergillus oryzae* untransformed transformation host MT3568 did not produce a noticeable clearing zone. The remaining culture EXP03899 fluid was filtered though a Fast PES Bottle top filter with a 0.22 μm cut-off.and stored in aliquots at −20° C. until further use.

Example 3: Cloning and Characterization of Two *Acremonioum alkalophilum* GH24 Lysozyme Encoding Genes (SEQ ID NOs: 4 and 6)

Genomic sequence information was generated by the U.S. Department of Energy Joint Genome Institute (JGI). According to Central Bureau vor Schnimmelkulture, *Acremonium alkalophilum* CBS 114.92 was isolated by A. Yoneda in 1984 from the sludge of pig faeces compost near Tsukui Lake, Japan. A preliminary assembly of the genome was downloaded from JGI and analyzed using the Pedant-Pro™ Sequence Analysis Suite (Biomax Informatics AG, Martinsried, Germany). Gene models constructed by the software were used as a starting point for detecting GH24 homologues in the genome. More precise gene models were constructed manually using multiple known GH24 protein sequences as a guide.

*Acremonium alkalophilum* CBS 114.92 was propagated on Horikoshi agar, pH9 for 7 days at 30° C. Mycelia was harvested directly from the plate and DNA was isolated according to the FastDNA SPIN Kit for Soil (www.mpbio.com). The DNA was eluted in 100 ul 10 mM TRIS buffer, 0.1 mM EDTA, pH 7, 5 and stored at 4° C. until use.

The pairs of synthetic oligonucleotide primers shown in table 2 below were designed to PCR amplify the *A. alkalophilum* CBS114.92 P242MS GH24 gene or P244A7 GH24 gene from the *A. alkalophilum* genomic DNA described in example 2 above.

TABLE 2

Primers used for GH24 and GH25 PCR Amplification

| GH24 gene | Specific forward primer | Specific reverse primer |
|---|---|---|
| A. alkalophilum CBS 114.92 GH24 P242MS | F-P242MS 5'-ACACAACTGGGG ATCCACCATGGCCAA GGTCTCTACCCT-3' (SEQ ID NO: 11) | R-P242MS 5'-AGATCTCGAGAA GCTTACTAAGAACAA GCAGGGAGGGC-3' (SEQ ID NO: 12) |
| A. alkalophilum CBS 114.92 GH24 P244A7 | F-P244A7 5'-ACACAACTGGGG ATCCACCATGGTCTC TTTCAAGCAGCTC-3' (SEQ ID NO: 13) | R-P244A7 5'-AGATCTCGAGAAG CTTACTAAGAGCAAGC AGGCAGAGC-3' (SEQ ID NO: 14) |

Bold letters represent coding sequence. The underlined sequence is homologous to the insertion sites of pDau109.

DNA sequencing of the *Acremonium alkalophilum* CBS114.92 GH24 genomic clones were performed with an Applied Biosystems Model 3730xl Automated DNA Sequencer using version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA). The sequences obtained were identical to the sequences from the JGI.

P242MS GH24 Gene

The nucleotide sequence and deduced amino acid sequence of the *Acremonium alkalophilum* GH24 gene are shown in SEQ ID NO: 3 and SEQ ID NO: 4, respectively. The coding sequence is 628 bp including the stop codon and is interrupted by a single intron of 67 bp (nucleotides 268 to 334). The encoded predicted protein is 186 amino acids. Using the SignalP program (Nielsen et al., 1997, Protein Engineering 10: 1-6), a signal peptide of 20 residues was predicted. The predicted mature protein contains 166 amino acids.

P244A7 GH24 Gene

The nucleotide sequence and deduced amino acid sequence of the *Acremonium alkalophilum* P244A7 GH24 gene are shown in SEQ ID NO: 5 and SEQ ID NO: 6, respectively. The coding sequence is 782 bp including the stop codon and is interrupted by two introns of 81 bp (nucleotides 134 to 214) and 170 bp (nucleotides 346-515). The encoded predicted protein is 176 amino acids. Using the SignalP program (Nielsen et al., 1997, *Protein Engineering* 10: 1-6), a signal peptide of 19 residues was predicted. The predicted mature protein contains 157 amino acids.

Plasmids for P242MS and P244A7 produced and transformed into *Aspergillus orzyzae* as in example 2. Transformants with culture fluids that produced recombinant protein product were identified by SDS-PAGE as in example 2 and designated: EXP03865, in the case of P242MS, and EXP03890 in the case of P244A7. Culture fluids from EXP03865 and EXP03890 fermented in both YP+2% glucose and DAP4C *media* were spotted on the xanthan bacterial cell debris plates. It was identified that DAP4C produced the best expression of the protein while YP+2% glucose produced the best expression for EXP03890 in both SDS-PAGE analysis and spot assay activity.

Example 4: RDA (Radial Diffusion Assays)

Initially, the antimicrobial activity of the culture supernatants and purified fractions containing the recombinantly expressed lysozymes was confirmed using an RDA's as described previously by Lehrer et al. (Lehrer et al., 1991, "Ultrasensitive assays for endogenous antimicrobial polypeptides", *J. Immunol. Methods* 137:167-73), with several modifications. Briefly, 30 mL of melted ⅒ Mueller-Hinton broth (MHB) (Sambrook et al., Molecular Cloning: A Laboratory Manual. Cold Spring Harbor: Cold Spring Harbor Laboratory Press, 1989) with 1% agarose was cooled to 42° C., supplemented to $5.0 \times 10^5$ cfu/mL with *S. carnosus* ATCC 51365 or *E. coli* DSM 682 (ATCC 10536) and was poured into a single-well omnitray (Nunc) plate. The omnitray plate was overlayed with a TSP plate (Nunc) and left to solidify. After 1 h, the TSP plate was removed; leaving 96 1-mm wells in which 10 μL of the compound of interest could be tested.

10 μl of the test solution is spotted pr. well and the plates are incubated O/N at 37° C. The following day clearing zones indicated no growth of test bacteria and thereby antimicrobial activity. The clearing zones were visualized by colouring with MTT (3-(4,5-dimethylthiazol-2-yl)-2,5-diphenyltetrazolium bromide, a yellow tetrazole), that is reduced to purple formazan in living cells (Mosmann, 1983, "Rapid colorimetric assay for cellular growth and survival: application to proliferation and cytotoxicity assays", *Journal of Immunological Methods* 65 (1-2): 55-63). This colouring provides for a dark colouring of living cells and no colouring of the clearing zones without living cells.

The *Aspergillus fumigatus* GH25 lysozyme (prepared as disclosed in Korczynska et al., 2010, *Acta Cryst.* F66, 973-977) was included in the test as a reference. The purified samples shown in table 3 below have been tested in the RDA assay.

TABLE 3

Radial Diffusion Assay of GH24 Lysozyme

| Lysozyme | Stock conc. | Dilution 0.7 ug/ul | Dilution 0.35 ug/ul |
|---|---|---|---|
| A. alcalophilum GH24 SEQ ID NO: 6 | 1.4 ug/ul | 37.5 ul enz. + 37.5 ul water | 18.8 ul enz. + 56.2 ul water |
| A. alcalophilum GH25 SEQ ID NO: 8 | 0.77 ug/ul | 68.2 ul enz. + 6.8 ul water | 34.1 ul enz. + 40.9 ul water |
| A. fumigatus GH25 (reference) | 12.2 ug/ul | 4.3 ul enz. + 70.6 ul water | 2.2 ul enz. + 72.8 ul water |

Measurement of Clearing Zones

The experiment was performed in triplicate with all resulting in same measured clearing zones/zones of inhibition, see FIG. 1. Table 4 below shows the clearing zones in mm.

TABLE 4

Antimicrobial Clearing Zones of GH24 Lysozyme Against *Staphylococcus carnosus* and *Escherichia coli*.

| | 0.7 µg/µl S. carnosus | 0.35 µg/µl S. carnosus | 0.7 µg/µl E. coli | 0.35 µg/µl E. coli |
|---|---|---|---|---|
| A. alcalophilum GH24 SEQ ID NO: 6 | 12 | 10 | 16 | 14 |
| A. alcalophilum GH25 SEQ ID NO: 8 | faint | faint | 8 (cloudy) | 6 (cloudy) |
| A. fumigatus GH25 (reference) | 11 | 10 | 10 | 8 |

The purified lysozyme having SEQ ID NO: 6 showed antimicrobial activity against viable cells of the gram positive bacteria *Staphylococcus carnosus* and the Gram negative bacteria *Escherichia coli*.

The antimicrobial activity is not present in culture supernatants from the untransformed *Aspergillus* production host (results not shown).

Large clearing zones with non defined borders were observed surrounding the application zone for *A. alcalophilum* GH24 (SEQ ID NO: 6). The experiment indicates that the *A. alcalophilum* lysozyme (SEQ ID NO: 6) and the *Aspergillus fumigatus* GH25 reference lysozyme have different activity and specificity against the two bacteria tested in this example.

Example 5: Turbidity Assay

The activity of lysozyme was determined by measuring the decrease (drop) in absorbance/optical density of a solution of resuspended *Micrococcus lysodeikticus* ATTC No. 4698 (Sigma-Aldrich M3770) or *Exiguobacterium undea* (DSM14481) measured in a spectrophotometer at 540 nm.

Preparation of *Micrococcus lysodeikticus* Substrate

Before use the cells were resuspended in citric acid—phosphate buffer pH 6.5 to a concentration of 0.5 mg cells/mL and the optical density (OD) at 540 nm was measured. The cell suspension was then adjusted so that the cell concentration equalled an OD540=1.0. The adjusted cell suspension was then stored cold before use. Resuspended cells were used within 4 hours.

Preparation of Citric Acid-Phosphate Buffer pH 6.5

29 mL 0.1 M citric acid was mixed with 61 mL 0.2 M $Na_2HPO_4$, and the pH was adjusted with HCl or NaOH to pH 6.5.

Preparation of Dried Cells of *Exiguobacterium undae* (the Substrate)

A culture of *E. undae* (DSM14481) was grown in 100 mL LB medium (Fluka 51208, 25 g/L) in a 500 mL shake-flask at 30° C., 250 rpm overnight. The overnight culture was then centrifuged at 20° C. and 5000 g for 10 minutes, and the pellet was washed two times in sterile milliQ water, and resuspended in Milli-Q water. The washed cells were centrifuged for 1 minute at 13000 rpm and as much as possible of the supernatant was decanted. The washed cells were dried in a vacuum centrifuge for 1 hour. The cell pellet was resuspended in citric acid—phosphate buffer pH 6.5 so that the optical density (OD) at 540 nm=1.

Measurement of Lysozyme Antimicrobial Activity in the Turbidity Assay

The lysozyme sample to be measured was diluted to a concentration of 100-200 mg enzyme protein/L in citric acid—phosphate buffer pH 6.5, and kept on ice until use. In a 96 well microtiterplate (Nunc) 200 µL of the substrate was added to each well, and the plate was incubated at 25° C. or 37° C. for 5 minutes in a VERSAmax microplate reader (Molecular Devices). Following incubation, the absorbance of each well was measured at 540 nm (start value). To start the activity measurement, 20 µL of the diluted lysozyme sample was added to each substrate (200 µL) and kinetic measurement of absorbance at 540 nm was initiated for minimum 30 minutes up to 24 hours at 25° C. or 37° C. The measured absorbance at 540 nm was monitored for each well and over time a drop in absorbance is seen if the lysozyme has lysozyme activity.

The *Aspergillus fumigatus* GH25 lysozyme (Korczynska et al., 2010, supra) was included in the test as a reference and the results are shown in table 5 below.

TABLE 5

Lysozyme Activity of GH25 Lysozymes against *Micrococcus lysodeikticus* and *Exiguobacterium undea* as measured by Optical Density Drop

| | *Micrococcus lysodeikticus* | *Exiguobacterium undae* | |
|---|---|---|---|
| Temperature | 37° C. | 25° C. | 37° C. |
| A. alcalophilum GH24 (SEQ ID NO: 4) | NT | − | − |
| A. alcalophilum GH24 (SEQ ID NO: 6) | +++ | + | + |

TABLE 5-continued

Lysozyme Activity of GH25 Lysozymes against *Micrococcus lysodeikticus* and *Exiguobacterium undea* as measured by Optical Density Drop

| | *Micrococcus lysodeikticus* | *Exiguobacterium undae* | |
|---|---|---|---|
| Temperature | 37° C. | 25° C. | 37° C. |
| *A. fumigatus* GH25 (reference) | + | +++ | +++ |

NT means not tested
− Means no effect
+ means small effect
++ means medium effect
+++ means large effect Example 6: Expression of P242MS GH24 Protein and P244A7 GH24 Protein in *Aspergillus oryzae*

The constructs comprising the relevant lysozyme gene were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The expression plasmids were transformed into *Aspergillus* as described in example 3. For each of the constructs 10-20 strains were isolated, purified and cultivated in shake flasks.

Example 7: Purification of P242MS GH24 Protein and P244A7 GH24 Protein in *Aspergillus oryzae*

Purification of P242MS GH24 Protein

The fermentation supernatant with the lysozyme was filtered through a Fast PES Bottle top filter with a 0.22 μm cut-off. pH was adjusted to 7.5 with 0.1 M NaOH and the resulting solution was concentrated (volume reduced by a factor of 8) on a Ultra Filtration Unit (Sartorius) with a 5 kDa cut-off membrane.

After pretreatment about 55 ml of the lysozyme containing solution was purified by chromatography on Q Sepharose, approximately 50 ml in a XK26 column, using as buffer A 50 mM TRIS pH 7.5, and as buffer B 50 mM TRIS+1 M NaCl pH 7.5. The fractions from the column were pooled based on the chromatogram (absorption at 280 and 254 nm) and SDS-PAGE analysis. The pooled fractions were buffer-changed into 50 mM Na-acetate, pH 5.5 and concentrated on a Vivacell 250 ml, 5 kDa PES filter.

The molecular weight, as estimated from SDS-PAGE, was approximately 20 kDa and the purity was >95%.

Purification of P244A7 GH24 Protein

The fermentation supernatant with the lysozyme was filtered through a sandwich of four Whatman glass microfiber filters (2.7, 1.6, 1.2 and 0.7 micrometer) and then through a Fast PES bottle top filter with a 0.22 μm cut-off. pH was adjusted to 4.5 with 10% acetic acid. After the pH-adjustment the solution became a little cloudy and this was removed by filtration through a Fast PES Bottle top filter with a 0.22 μm cut-off.

After pretreatment about 970 ml of the lysozyme containing solution was purified by chromatography on SP Sepharose, approximately 50 ml in a XK26 column, using as buffer A 50 mM Na-acetate pH 4.5, and as buffer B 50 mM Na-acetate+1 M NaCl pH 4.5. The fractions from the column were pooled based on the chromatogram (absorption at 280 and 254 nm) and SDS-PAGE analysis. The pooled fractions were buffer-changed into 50 mM Na-acetate, pH 5.5 and concentrated using Amicon spin filters with a 10 kDa cut-off.

The molecular weight, as estimated from SDS-PAGE, was approximately 20 kDa and the purity was >90%.

The invention claimed is:

1. A variant polypeptide having lysozyme activity, which has at least 95% sequence identity and comprises one or more amino acid substitutions to a sequence selected from the group consisting of amino acids 20 to 264 of SEQ ID NO: 2, amino acids 21 to 186 of SEQ ID NO: 4, and amino acids 20 to 176 of SEQ ID NO: 6.

2. The variant polypeptide of claim 1, which has at least 95% sequence identity to the sequence of amino acids 20 to 264 of SEQ ID NO: 2.

3. The variant polypeptide of claim 1, which has at least 97% sequence identity to the sequence of amino acids 20 to 264 of SEQ ID NO: 2.

4. The variant polypeptide of claim 1, which has at least 95% sequence identity to the sequence of amino acids 21 to 186 of SEQ ID NO: 4.

5. The variant polypeptide of claim 1, which has at least 97% sequence identity to the sequence of amino acids 21 to 186 of SEQ ID NO: 4.

6. The variant polypeptide of claim 1, which has at least 95% sequence identity to the sequence of amino acids 20 to 176 of SEQ ID NO: 6.

7. The variant polypeptide of claim 1, which has at least 97% sequence identity to the sequence of amino acids 20 to 176 of SEQ ID NO: 6.

8. A detergent composition comprising the variant polypeptide of claim 1 and a surfactant.

9. The detergent composition of claim 8, which further comprises one or more further enzymes selected from the group comprising of amylases, catalases, cellulases, cutinases, haloperoxygenases, lipases, mannanases, pectinases, pectin lyases, peroxidases, proteases, xanthanases, and xyloglucanases, or any mixture thereof.

10. The detergent composition of claim 8, further comprising of one or more components selected from the group consisting of builders, hydrotopes, bleaching systems, polymers, fabric hueing agents, adjunct materials, dispersants, dye transfer inhibiting agents, fluorescent whitening agents, soil release polymers and anti-redeposition agents.

11. An animal feed composition comprising the variant polypeptide of claim 1.

12. The animal feed composition of claim 11, which further comprises of one or more amylases; galactanases; alpha-galactosidases; beta-glucanases, phospholipases, phytases, proteases, and xylanases, or any mixture thereof.

13. An animal feed additive comprising
 (a) at least one variant polypeptide of claim 1; and
 (b) at least one fat-soluble vitamin, at least one water-soluble vitamin, and/or at least one trace mineral.

14. The animal feed additive of claim 13, which further comprises of one or more amylases, galactanases, alpha-galactosidases, beta-glucanases, phospholipases, phytases, proteases, and xylanases, or any mixture thereof.

* * * * *

SEQUENCE LISTING

<160> NUMBER OF SEQ ID NOS: 14

<210> SEQ ID NO 1
<211> LENGTH: 862
<212> TYPE: DNA
<213> ORGANISM: Aspergillus aculeatus
<220> FEATURE:
<221> NAME/KEY: CDS
<222> LOCATION: (1)..(571)
<220> FEATURE:
<221> NAME/KEY: sig_peptide
<222> LOCATION: (1)..(57)
<220> FEATURE:
<221> NAME/KEY: CDS
<222> LOCATION: (639)..(859)

<400> SEQUENCE: 1

```
atg cag ttg aac aac ttc ctt ctg gcc gcc gcc act ctg gtc ggc ctc      48
Met Gln Leu Asn Asn Phe Leu Leu Ala Ala Ala Thr Leu Val Gly Leu
1               5                   10                  15 tcc gcc gct gtc ccc atg ggc agt cgg act aag aac ctg gcc acc cgc      96
Ser Ala Ala Val Pro Met Gly Ser Arg Thr Lys Asn Leu Ala Thr Arg
            20                  25                  30 gcc acc aat gcc gtg gtc agc gtc agc agc ctg gcc gcg acc acg ctc     144
```

```
Ala Thr Asn Ala Val Val Ser Val Ser Ser Leu Ala Ala Thr Thr Leu
             35                  40                  45 aag gac aac gac ggc agc gga gcc gga cag gat gtc tac acc ttc cac      192
Lys Asp Asn Asp Gly Ser Gly Ala Gly Gln Asp Val Tyr Thr Phe His
 50                  55                  60 acc gga gac ggc agc gtc gcc gac ggc tgg ccc gcc cag tcc agc tgg      240
Thr Gly Asp Gly Ser Val Ala Asp Gly Trp Pro Ala Gln Ser Ser Trp
 65                  70                  75                  80 gtc tcc ttc gac gac atg tgg aag gcc aac aag ccc acc atc atg gag      288
Val Ser Phe Asp Asp Met Trp Lys Ala Asn Lys Pro Thr Ile Met Glu
                 85                  90                  95 tcg tgc acc cag ttc ggc gtg ccc aac aac tcg gcc aac gag acc cag      336
Ser Cys Thr Gln Phe Gly Val Pro Asn Asn Ser Ala Asn Glu Thr Gln
            100                 105                 110 aac ctg tac gac gcg atc cag cag gtg gcc aag gag tcc cac ctc gac      384
Asn Leu Tyr Asp Ala Ile Gln Gln Val Ala Lys Glu Ser His Leu Asp
        115                 120                 125 cac cgg ttc atc ctg gcc atc atc atg cag gaa tcc aag ggc tgc gtc      432
His Arg Phe Ile Leu Ala Ile Ile Met Gln Glu Ser Lys Gly Cys Val
130                 135                 140 cgc gtg cac acc acc aac tac ggc gtc cgc aac ccg ggc ctc atg cag      480
Arg Val His Thr Thr Asn Tyr Gly Val Arg Asn Pro Gly Leu Met Gln
145                 150                 155                 160 gat cat gat ggc gcc ggc act tgc aac gac aac ggg gtg gtc cag aac      528
Asp His Asp Gly Ala Gly Thr Cys Asn Asp Asn Gly Val Val Gln Asn
                165                 170                 175 ccg tgc ccc aag aac gag atc ctc cag atg gtt cgc gat ggg g            571
Pro Cys Pro Lys Asn Glu Ile Leu Gln Met Val Arg Asp Gly
            180                 185                 190 gtgagtgtcc cttccaaccc tcccaatctc ctttcagcgc agacactaat ccccctcctct   631 cacacag cc atc gga acc gcc gcc ggc gac gga ctg gcc agt ctg atc       679
            Ala Ile Gly Thr Ala Ala Gly Asp Gly Leu Ala Ser Leu Ile
                            195                 200 gac cag cag ggc aag acg gac gtc tcc ggc ttt tac cgc gcc gcc cgc      727
Asp Gln Gln Gly Lys Thr Asp Val Ser Gly Phe Tyr Arg Ala Ala Arg
205                 210                 215                 220 ctg tac aac tcg ggc tcc atc tcc gac gcc tcc aac ctg aac gtc ggc      775
Leu Tyr Asn Ser Gly Ser Ile Ser Asp Ala Ser Asn Leu Asn Val Gly
                225                 230                 235 gtc ggc acc gcc tgc tac gcc acc gat gtt gcc aac cgg ctc acc ggc      823
Val Gly Thr Ala Cys Tyr Ala Thr Asp Val Ala Asn Arg Leu Thr Gly
            240                 245                 250 tgg gtc aac gcc gcc tcc aag tgc acc ctg agc gca tag                  862
Trp Val Asn Ala Ala Ser Lys Cys Thr Leu Ser Ala
255                 260

<210> SEQ ID NO 2
<211> LENGTH: 264
<212> TYPE: PRT
<213> ORGANISM: Aspergillus aculeatus

<400> SEQUENCE: 2

Met Gln Leu Asn Asn Phe Leu Leu Ala Ala Ala Thr Leu Val Gly Leu
 1               5                  10                  15

Ser Ala Ala Val Pro Met Gly Ser Arg Thr Lys Asn Leu Ala Thr Arg
             20                  25                  30

Ala Thr Asn Ala Val Val Ser Val Ser Ser Leu Ala Ala Thr Thr Leu
             35                  40                  45

Lys Asp Asn Asp Gly Ser Gly Ala Gly Gln Asp Val Tyr Thr Phe His
 50                  55                  60
```

```
                        50                  55                  60
Thr Gly Asp Gly Ser Val Ala Asp Gly Trp Pro Ala Gln Ser Ser Trp
 65                  70                  75                  80

Val Ser Phe Asp Asp Met Trp Lys Ala Asn Lys Pro Thr Ile Met Glu
                 85                  90                  95

Ser Cys Thr Gln Phe Gly Val Pro Asn Asn Ser Ala Asn Glu Thr Gln
                100                 105                 110

Asn Leu Tyr Asp Ala Ile Gln Gln Val Ala Lys Glu Ser His Leu Asp
            115                 120                 125

His Arg Phe Ile Leu Ala Ile Ile Met Gln Glu Ser Lys Gly Cys Val
        130                 135                 140

Arg Val His Thr Thr Asn Tyr Gly Val Arg Asn Pro Gly Leu Met Gln
145                 150                 155                 160

Asp His Asp Gly Ala Gly Thr Cys Asn Asp Asn Gly Val Val Gln Asn
                165                 170                 175

Pro Cys Pro Lys Asn Glu Ile Leu Gln Met Val Arg Asp Gly Ala Ile
            180                 185                 190

Gly Thr Ala Ala Gly Asp Gly Leu Ala Ser Leu Ile Asp Gln Gln Gly
        195                 200                 205

Lys Thr Asp Val Ser Gly Phe Tyr Arg Ala Ala Arg Leu Tyr Asn Ser
210                 215                 220

Gly Ser Ile Ser Asp Ala Ser Asn Leu Asn Val Gly Val Gly Thr Ala
225                 230                 235                 240

Cys Tyr Ala Thr Asp Val Ala Asn Arg Leu Thr Gly Trp Val Asn Ala
                245                 250                 255

Ala Ser Lys Cys Thr Leu Ser Ala
            260

<210> SEQ ID NO 3
<211> LENGTH: 628
<212> TYPE: DNA
<213> ORGANISM: Acremonium alcalophilum
<220> FEATURE:
<221> NAME/KEY: CDS
<222> LOCATION: (1)..(267)
<220> FEATURE:
<221> NAME/KEY: sig_peptide
<222> LOCATION: (1)..(60)
<220> FEATURE:
<221> NAME/KEY: CDS
<222> LOCATION: (335)..(625)

<400> SEQUENCE: 3 atg gcc aag gtc tct acc ctc acc atc gca ctc ctc acc atg gcc tcc      48
Met Ala Lys Val Ser Thr Leu Thr Ile Ala Leu Leu Thr Met Ala Ser
 1               5                  10                  15 cag gct cgc gcg cag tgc gtc ggt ccc gag gtt aac agc gcc agc atc      96
Gln Ala Arg Ala Gln Cys Val Gly Pro Glu Val Asn Ser Ala Ser Ile
                20                  25                  30 aac ctc atc aaa gag ttt gag ggc tgg tat ccc gac atc tac gtc gat     144
Asn Leu Ile Lys Glu Phe Glu Gly Trp Tyr Pro Asp Ile Tyr Val Asp
            35                  40                  45 ccc gcc ggc tat ccg acc gtc ggc tac ggc cac ctc tgc tcc gac tcg     192
Pro Ala Gly Tyr Pro Thr Val Gly Tyr Gly His Leu Cys Ser Asp Ser
        50                  55                  60 agc tgt tcc gac gtg tcg tac tcc att ccg ttg tcc gag gcg gac ggc     240
Ser Cys Ser Asp Val Ser Tyr Ser Ile Pro Leu Ser Glu Ala Asp Gly
 65                 70                  75                  80 gag aat ctc ctc cgt gac gac att acc gtgcgttggc ccttcttct            287
```

```
                Glu Asn Leu Leu Arg Asp Asp Ile Thr
                                85 ttccactttt cccaagaaga agaaggagaa attactaatg tccaaag aac ttc caa        343
                                                 Asn Phe Gln
                                                      90 aac tgc atc acc tgg cag acc gcc tcg tcc gtc gtc ctc aac gcc aac        391
Asn Cys Ile Thr Trp Gln Thr Ala Ser Ser Val Val Leu Asn Ala Asn
     95              100                 105 cag tat ggc gcc ctc gtc tcg tgg gcc ttc aac gta ggc tgt ggc gcc        439
Gln Tyr Gly Ala Leu Val Ser Trp Ala Phe Asn Val Gly Cys Gly Ala
        110              115                 120 tct gag tct tcg tcg ctg atc gcc cgc ctc aac gcc ggc gag gac ccc        487
Ser Glu Ser Ser Ser Leu Ile Ala Arg Leu Asn Ala Gly Glu Asp Pro
125                 130                 135                 140 aac acc gtc gcc gag gag gag ctg ccg cgg tgg aac cag ggt ggc ggc        535
Asn Thr Val Ala Glu Glu Glu Leu Pro Arg Trp Asn Gln Gly Gly Gly
                145                 150                 155 cag gtc ctc ccc ggt ctt gtc cgt cgt cgc gcc gcc gag gtc gag ctg        583
Gln Val Leu Pro Gly Leu Val Arg Arg Arg Ala Ala Glu Val Glu Leu
            160                 165                 170 cac cag att cct act gac gtg gcc gcc ctc cct gct tgt tct tag            628
His Gln Ile Pro Thr Asp Val Ala Ala Leu Pro Ala Cys Ser
        175                 180                 185

<210> SEQ ID NO 4
<211> LENGTH: 186
<212> TYPE: PRT
<213> ORGANISM: Acremonium alcalophilum

<400> SEQUENCE: 4

Met Ala Lys Val Ser Thr Leu Thr Ile Ala Leu Leu Thr Met Ala Ser
1               5                   10                  15

Gln Ala Arg Ala Gln Cys Val Gly Pro Glu Val Asn Ser Ala Ser Ile
            20                  25                  30

Asn Leu Ile Lys Glu Phe Glu Gly Trp Tyr Pro Asp Ile Tyr Val Asp
        35                  40                  45

Pro Ala Gly Tyr Pro Thr Val Gly Tyr Gly His Leu Cys Ser Asp Ser
    50                  55                  60

Ser Cys Ser Asp Val Ser Tyr Ser Ile Pro Leu Ser Glu Ala Asp Gly
65                  70                  75                  80

Glu Asn Leu Leu Arg Asp Asp Ile Thr Asn Phe Gln Asn Cys Ile Thr
                85                  90                  95

Trp Gln Thr Ala Ser Ser Val Val Leu Asn Ala Asn Gln Tyr Gly Ala
            100                 105                 110

Leu Val Ser Trp Ala Phe Asn Val Gly Cys Gly Ala Ser Glu Ser Ser
        115                 120                 125

Ser Leu Ile Ala Arg Leu Asn Ala Gly Glu Asp Pro Asn Thr Val Ala
    130                 135                 140

Glu Glu Glu Leu Pro Arg Trp Asn Gln Gly Gly Gly Gln Val Leu Pro
145                 150                 155                 160

Gly Leu Val Arg Arg Arg Ala Ala Glu Val Glu Leu His Gln Ile Pro
                165                 170                 175

Thr Asp Val Ala Ala Leu Pro Ala Cys Ser
            180                 185

<210> SEQ ID NO 5
<211> LENGTH: 782
<212> TYPE: DNA
```

```
<213> ORGANISM: Acremonium alcalophilum
<220> FEATURE:
<221> NAME/KEY: CDS
<222> LOCATION: (1)..(133)
<220> FEATURE:
<221> NAME/KEY: sig_peptide
<222> LOCATION: (1)..(57)
<220> FEATURE:
<221> NAME/KEY: CDS
<222> LOCATION: (215)..(345)
<220> FEATURE:
<221> NAME/KEY: CDS
<222> LOCATION: (516)..(779)

<400> SEQUENCE: 5
```

| atg | gtc | tct | ttc | aag | cag | ctc | gcc | ctc | ctg | gca | ctg | ggc | gcc | gtc | caa | 48 |
|---|---|---|---|---|---|---|---|---|---|---|---|---|---|---|---|---|
| Met | Val | Ser | Phe | Lys | Gln | Leu | Ala | Leu | Leu | Ala | Leu | Gly | Ala | Val | Gln | |
| 1 | | | | 5 | | | | | 10 | | | | | 15 | | |

| gta | cag | gcg | cag | tgc | gtc | ggc | ccg | gct | atc | aat | tcc | gcg | gct | ctt | aac | 96 |
|---|---|---|---|---|---|---|---|---|---|---|---|---|---|---|---|---|
| Val | Gln | Ala | Gln | Cys | Val | Gly | Pro | Ala | Ile | Asn | Ser | Ala | Ala | Leu | Asn | |
| | | 20 | | | | | 25 | | | | | 30 | | | | |

| ctc | atc | aag | gag | ttt | gag | gga | tgg | agg | ccc | aac | att | t | gtgcgttccc | 143 |
|---|---|---|---|---|---|---|---|---|---|---|---|---|---|---|
| Leu | Ile | Lys | Glu | Phe | Glu | Gly | Trp | Arg | Pro | Asn | Ile | | | |
| | 35 | | | | | 40 | | | | | | | | | ttctacgtta catcacccag ttccttgtt attcagacat tatttctata ttcctggcta 203

| acactgtaaa | g | ac | cgc | gac | ccc | gtc | ggc | ctc | ccc | acc | gtc | gga | tac | ggc | 252 |
|---|---|---|---|---|---|---|---|---|---|---|---|---|---|---|---|
| | | | Tyr | Arg | Asp | Pro | Val | Gly | Leu | Pro | Thr | Val | Gly | Tyr | Gly | |
| | | | | 45 | | | | | 50 | | | | | 55 | | |

| cac | ctc | tgc | cgc | gac | tcg | agc | tgc | tct | gac | gtc | cct | tac | cca | att | ccc | 300 |
|---|---|---|---|---|---|---|---|---|---|---|---|---|---|---|---|---|
| His | Leu | Cys | Arg | Asp | Ser | Ser | Cys | Ser | Asp | Val | Pro | Tyr | Pro | Ile | Pro | |
| | | 60 | | | | | 65 | | | | | 70 | | | | |

| ctg | tcc | gtt | gcc | aac | ggc | gag | cgt | ctc | ctt | cgg | agc | gac | cta | gcg | 345 |
|---|---|---|---|---|---|---|---|---|---|---|---|---|---|---|---|
| Leu | Ser | Val | Ala | Asn | Gly | Glu | Arg | Leu | Leu | Arg | Ser | Asp | Leu | Ala | |
| 75 | | | | | 80 | | | | | 85 | | | | | | gtgagtctat ccctttgca cttcataaaa cgtcgccttc tctgttgtca ttctacctgg 405 acagcctccc cctatttctc tcttctatct tttcttcttt cccgttctgc aagcttgacc 465

| cctgaccaac | catatccacc | cagacctacc | agaactgcat | cacgatgcag | acg | gcc | 521 |
|---|---|---|---|---|---|---|---|
| | | | | | Thr | Ala | |
| | | | | | | 90 | |

| tcg | tcc | gtc | gtc | ctg | aat | gcg | aac | cag | tac | ggc | gcc | ctg | gtc | agc | tgg | 569 |
|---|---|---|---|---|---|---|---|---|---|---|---|---|---|---|---|---|
| Ser | Ser | Val | Val | Leu | Asn | Ala | Asn | Gln | Tyr | Gly | Ala | Leu | Val | Ser | Trp | |
| | | | 95 | | | | | 100 | | | | | 105 | | | |

| gcc | ttc | aac | gtc | ggc | tgc | ggc | gcc | acc | agc | acg | tcg | act | ctg | atc | cgc | 617 |
|---|---|---|---|---|---|---|---|---|---|---|---|---|---|---|---|---|
| Ala | Phe | Asn | Val | Gly | Cys | Gly | Ala | Thr | Ser | Thr | Ser | Thr | Leu | Ile | Arg | |
| | | 110 | | | | | 115 | | | | | 120 | | | | |

| cgc | ctc | aac | gcc | gga | gag | agc | ccc | aac | acc | gtc | gct | gcc | cag | gag | ctg | 665 |
|---|---|---|---|---|---|---|---|---|---|---|---|---|---|---|---|---|
| Arg | Leu | Asn | Ala | Gly | Glu | Ser | Pro | Asn | Thr | Val | Ala | Ala | Gln | Glu | Leu | |
| | 125 | | | | | 130 | | | | | 135 | | | | | |

| cct | cgc | tgg | aac | aag | gct | ggc | ggc | cag | gtc | ctg | ccc | ggc | ctg | gtg | cgc | 713 |
|---|---|---|---|---|---|---|---|---|---|---|---|---|---|---|---|---|
| Pro | Arg | Trp | Asn | Lys | Ala | Gly | Gly | Gln | Val | Leu | Pro | Gly | Leu | Val | Arg | |
| 140 | | | | 145 | | | | | 150 | | | | | | | |

| cgc | cgt | gct | gcc | gag | gta | gag | ctg | cat | cgt | act | tcc | acc | agt | gtc | cgt | 761 |
|---|---|---|---|---|---|---|---|---|---|---|---|---|---|---|---|---|
| Arg | Arg | Ala | Ala | Glu | Val | Glu | Leu | His | Arg | Thr | Ser | Thr | Ser | Val | Arg | |
| 155 | | | | | 160 | | | | | 165 | | | | | 170 | |

| gct | ctg | cct | gct | tgc | tct | tag | 782 |
|---|---|---|---|---|---|---|---|
| Ala | Leu | Pro | Ala | Cys | Ser | | |
| | | 175 | | | | | |

```
<210> SEQ ID NO 6
<211> LENGTH: 176
<212> TYPE: PRT
<213> ORGANISM: Acremonium alcalophilum
```

-continued

<400> SEQUENCE: 6

Met Val Ser Phe Lys Gln Leu Ala Leu Leu Ala Leu Gly Ala Val Gln
1               5                   10                  15

Val Gln Ala Gln Cys Val Gly Pro Ala Ile Asn Ser Ala Ala Leu Asn
            20                  25                  30

Leu Ile Lys Glu Phe Glu Gly Trp Arg Pro Asn Ile Tyr Arg Asp Pro
        35                  40                  45

Val Gly Leu Pro Thr Val Gly Tyr Gly His Leu Cys Arg Asp Ser Ser
    50                  55                  60

Cys Ser Asp Val Pro Tyr Pro Ile Pro Leu Ser Val Ala Asn Gly Glu
65                  70                  75                  80

Arg Leu Leu Arg Ser Asp Leu Ala Thr Ala Ser Ser Val Val Leu Asn
                85                  90                  95

Ala Asn Gln Tyr Gly Ala Leu Val Ser Trp Ala Phe Asn Val Gly Cys
            100                 105                 110

Gly Ala Thr Ser Thr Ser Thr Leu Ile Arg Arg Leu Asn Ala Gly Glu
        115                 120                 125

Ser Pro Asn Thr Val Ala Ala Gln Glu Leu Pro Arg Trp Asn Lys Ala
    130                 135                 140

Gly Gly Gln Val Leu Pro Gly Leu Val Arg Arg Ala Ala Glu Val
145                 150                 155                 160

Glu Leu His Arg Thr Ser Thr Ser Val Arg Ala Leu Pro Ala Cys Ser
                165                 170                 175

<210> SEQ ID NO 7
<211> LENGTH: 838
<212> TYPE: DNA
<213> ORGANISM: Acremonium alcalophilum
<220> FEATURE:
<221> NAME/KEY: CDS
<222> LOCATION: (1)..(147)
<220> FEATURE:
<221> NAME/KEY: sig_peptide
<222> LOCATION: (1)..(57)
<220> FEATURE:
<221> NAME/KEY: CDS
<222> LOCATION: (302)..(835)

<400> SEQUENCE: 7

```
atg aag ctt ctt ccc tcc ttg att ggc ctg gcc agt ctg gcg tcc ctc      48
Met Lys Leu Leu Pro Ser Leu Ile Gly Leu Ala Ser Leu Ala Ser Leu
1               5                   10                  15 gcc gtc gcc cgg atc ccc ggc ttt gac att tcg ggc tgg caa ccg acc      96
Ala Val Ala Arg Ile Pro Gly Phe Asp Ile Ser Gly Trp Gln Pro Thr
            20                  25                  30 acc gac ttt gca agg gcg tat gct aat gga gat cgt ttc gtc tac atc     144
Thr Asp Phe Ala Arg Ala Tyr Ala Asn Gly Asp Arg Phe Val Tyr Ile
        35                  40                  45 aag gtacgttcaa ccttgccacc aagttgcgaa cccgagacaa gactgtgacc           197
Lys gcctcctttg ccctggggca gctcacgcac ccagcagcat cccatccccc ggccccccac   257
gtaccaccgg aaagctaaca tcaaccccct accactgcta ccag gcc acc gag ggc    313
                                                 Ala Thr Glu Gly
                                                         50 acc aca ttc aag agc tcc gca ttc agc cgc cag tac acc ggc gca acg     361
Thr Thr Phe Lys Ser Ser Ala Phe Ser Arg Gln Tyr Thr Gly Ala Thr
        55                  60                  65 caa aac ggc ttc atc cgc ggc gcc tac cac ttc gcc cag ccc gcc gcg     409
```

```
                Gln Asn Gly Phe Ile Arg Gly Ala Tyr His Phe Ala Gln Pro Ala Ala
                 70                  75                  80                  85 tcg tcg ggc gcc gcg cag gcg aga tac ttc gcc agc aac ggc ggc ggc              457
Ser Ser Gly Ala Ala Gln Ala Arg Tyr Phe Ala Ser Asn Gly Gly Gly
                 90                  95                 100 tgg tcc aag gac ggc atc acc ctg ccc ggg gcg ctg gac atc gag tac              505
Trp Ser Lys Asp Gly Ile Thr Leu Pro Gly Ala Leu Asp Ile Glu Tyr
            105                 110                 115 aac ccc aac ggc gcc acc tgc tac ggc ctc tcg caa tcg gcc atg gtg              553
Asn Pro Asn Gly Ala Thr Cys Tyr Gly Leu Ser Gln Ser Ala Met Val
        120                 125                 130 aac tgg atc gag gac ttt gtc acc acc tac cac ggc atc acc tcc cgc              601
Asn Trp Ile Glu Asp Phe Val Thr Thr Tyr His Gly Ile Thr Ser Arg
    135                 140                 145 tgg ccc gtc atc tac acc acc acc gac tgg tgg acc cag tgc acc ggc              649
Trp Pro Val Ile Tyr Thr Thr Thr Asp Trp Trp Thr Gln Cys Thr Gly
150                 155                 160                 165 aac tcc aac cgc ttc gcg aac cgc tgc ccg ctg tgg atc gcc cgc tac              697
Asn Ser Asn Arg Phe Ala Asn Arg Cys Pro Leu Trp Ile Ala Arg Tyr
                170                 175                 180 gcc agc tcc gtc ggc act ctg ccc aat ggc tgg ggc ttt tac acc ttc              745
Ala Ser Ser Val Gly Thr Leu Pro Asn Gly Trp Gly Phe Tyr Thr Phe
            185                 190                 195 tgg cag tac aac gac aag tat cct cag ggc ggt gat tcg aac tgg ttc              793
Trp Gln Tyr Asn Asp Lys Tyr Pro Gln Gly Gly Asp Ser Asn Trp Phe
        200                 205                 210 aac ggc gat gcg tcg cgt ctc agg gct ctc gct aac gga gac taa                  838
Asn Gly Asp Ala Ser Arg Leu Arg Ala Leu Ala Asn Gly Asp
    215                 220                 225

<210> SEQ ID NO 8
<211> LENGTH: 227
<212> TYPE: PRT
<213> ORGANISM: Acremonium alcalophilum

<400> SEQUENCE: 8

Met Lys Leu Leu Pro Ser Leu Ile Gly Leu Ala Ser Leu Ala Ser Leu
1               5                   10                  15

Ala Val Ala Arg Ile Pro Gly Phe Asp Ile Ser Gly Trp Gln Pro Thr
            20                  25                  30

Thr Asp Phe Ala Arg Ala Tyr Ala Asn Gly Asp Arg Phe Val Tyr Ile
        35                  40                  45

Lys Ala Thr Glu Gly Thr Thr Phe Lys Ser Ser Ala Phe Ser Arg Gln
    50                  55                  60

Tyr Thr Gly Ala Thr Gln Asn Gly Phe Ile Arg Gly Ala Tyr His Phe
65                  70                  75                  80

Ala Gln Pro Ala Ala Ser Ser Gly Ala Ala Gln Ala Arg Tyr Phe Ala
                85                  90                  95

Ser Asn Gly Gly Gly Trp Ser Lys Asp Gly Ile Thr Leu Pro Gly Ala
            100                 105                 110

Leu Asp Ile Glu Tyr Asn Pro Asn Gly Ala Thr Cys Tyr Gly Leu Ser
        115                 120                 125

Gln Ser Ala Met Val Asn Trp Ile Glu Asp Phe Val Thr Thr Tyr His
    130                 135                 140

Gly Ile Thr Ser Arg Trp Pro Val Ile Tyr Thr Thr Thr Asp Trp Trp
145                 150                 155                 160

Thr Gln Cys Thr Gly Asn Ser Asn Arg Phe Ala Asn Arg Cys Pro Leu
                165                 170                 175
```

```
Trp Ile Ala Arg Tyr Ala Ser Ser Val Gly Thr Leu Pro Asn Gly Trp
            180                 185                 190

Gly Phe Tyr Thr Phe Trp Gln Tyr Asn Asp Lys Tyr Pro Gln Gly Gly
        195                 200                 205

Asp Ser Asn Trp Phe Asn Gly Asp Ala Ser Arg Leu Arg Ala Leu Ala
    210                 215                 220

Asn Gly Asp
225

<210> SEQ ID NO 9
<211> LENGTH: 42
<212> TYPE: DNA
<213> ORGANISM: Artificial sequence
<220> FEATURE:
<223> OTHER INFORMATION: Primer F-P8EH

<400> SEQUENCE: 9
acacaactgg ggatccacca tgcagttgaa caacttcctt ct                    42

<210> SEQ ID NO 10
<211> LENGTH: 37
<212> TYPE: DNA
<213> ORGANISM: Artificial sequence
<220> FEATURE:
<223> OTHER INFORMATION: Primer R-F8EH

<400> SEQUENCE: 10
agatctcgag aagcttacta tgcgctcagg gtgcact                          37

<210> SEQ ID NO 11
<211> LENGTH: 39
<212> TYPE: DNA
<213> ORGANISM: Artificial sequence
<220> FEATURE:
<223> OTHER INFORMATION: Primer F-P242MS

<400> SEQUENCE: 11
acacaactgg ggatccacca tggccaaggt ctctaccct                        39

<210> SEQ ID NO 12
<211> LENGTH: 38
<212> TYPE: DNA
<213> ORGANISM: Artificial sequence
<220> FEATURE:
<223> OTHER INFORMATION: Primer R-P242MS

<400> SEQUENCE: 12
agatctcgag aagcttacta agaacaagca gggagggc                         38

<210> SEQ ID NO 13
<211> LENGTH: 40
<212> TYPE: DNA
<213> ORGANISM: Artificial sequence
<220> FEATURE:
<223> OTHER INFORMATION: Primer F-P244A7

<400> SEQUENCE: 13
acacaactgg ggatccacca tggtctcttt caagcagctc                       40

<210> SEQ ID NO 14
<211> LENGTH: 38
<212> TYPE: DNA
<213> ORGANISM: Artificial sequence
<220> FEATURE:
```

```
<223> OTHER INFORMATION: Primer R-P244A7

<400> SEQUENCE: 14
agatctcgag aagcttacta agagcaagca ggcagagc                              38
```